US010464982B2

(12) United States Patent
Galipeau et al.

(10) Patent No.: US 10,464,982 B2
(45) Date of Patent: Nov. 5, 2019

(54) COMPOSITIONS OF GM-CSF AND INTERLEUKIN FUSIONS FOR IMMUNE MODULATION AND USES RELATED THERETO

(71) Applicants: Emory University, Atlanta, GA (US); Children's Healthcare of Atlanta, Inc., Atlanta, GA (US)

(72) Inventors: Jacques Galipeau, Atlanta, GA (US); Andrea Pennati, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 182 days.

(21) Appl. No.: 15/305,714

(22) PCT Filed: Apr. 13, 2015

(86) PCT No.: PCT/US2015/025514
§ 371 (c)(1),
(2) Date: Oct. 21, 2016

(87) PCT Pub. No.: WO2015/164107
PCT Pub. Date: Oct. 29, 2015

(65) Prior Publication Data
US 2017/0073387 A1  Mar. 16, 2017

Related U.S. Application Data

(60) Provisional application No. 61/982,912, filed on Apr. 23, 2014.

(51) Int. Cl.
*A61K 38/19* (2006.01)
*A61K 38/20* (2006.01)
*C07K 14/535* (2006.01)
*A61K 35/17* (2015.01)
*C07K 14/54* (2006.01)
*C07K 14/55* (2006.01)
*A61K 39/00* (2006.01)
*A61K 45/06* (2006.01)
*A61K 38/00* (2006.01)

(52) U.S. Cl.
CPC ............ *C07K 14/535* (2013.01); *A61K 35/17* (2013.01); *A61K 39/0008* (2013.01); *A61K 45/06* (2013.01); *C07K 14/5406* (2013.01); *C07K 14/5425* (2013.01); *C07K 14/5443* (2013.01); *C07K 14/55* (2013.01); *A61K 38/00* (2013.01); *A61K 2039/515* (2013.01); *C07K 2319/00* (2013.01)

(58) Field of Classification Search
None
See application file for complete search history.

(56) References Cited

U.S. PATENT DOCUMENTS

| 7,947,265 | B2 * | 5/2011 | Galipeau ............. A61K 38/193 424/85.1 |
|---|---|---|---|
| 8,013,124 | B2 | 9/2011 | Sprecher |
| 8,163,879 | B2 | 4/2012 | Wong |
| 8,383,775 | B2 | 2/2013 | Novak |
| 8,586,055 | B2 | 11/2013 | Felber |
| 8,647,866 | B2 | 2/2014 | Sprecher |
| 8,771,664 | B2 | 7/2014 | Lopez |
| 2005/0053579 | A1 | 3/2005 | Galipeau |
| 2006/0251619 | A1 * | 11/2006 | Borrelly ................ C07K 14/57 424/85.6 |
| 2006/0269526 | A1 | 11/2006 | Galipeau |
| 2010/0021421 | A1 | 1/2010 | Galipeau |
| 2011/0177070 | A1 | 7/2011 | Lofquist |
| 2018/0155439 | A1 | 6/2018 | Galipeau |

FOREIGN PATENT DOCUMENTS

| WO | 2005100395 | 10/2005 |
|---|---|---|
| WO | 2012040323 | 3/2012 |

OTHER PUBLICATIONS

Peti et al. FEBS J., vol. 280 (2) pp. 596-611 (Year: 2013).*
Tropea et al. Methods in Molecular Biology: High throughput Protein Expression and Purification, vol. 498, pp. 297-307 (Year: 2009).*
Benahmed et al. Inhibition of TGF-beta Signaling by IL-15: A New Role for IL-15 in the Loss of Immune Homeostasis in Celiac Disease, Gastroenterology 2007, 132:994-1008.
Bessard et al. High antitumor activity of RLI, an interleukin-15 (IL-15)—IL-15 receptor a fusion protein, in metastatic melanoma and colorectal cancer, Mol Cancer Ther 2009,8(9).
Chou et al. Effects of immunotherapy of IL-6 and IL-15 plasmids on transmissible venereal tumor in beagles, Veterinary Immunology and Immunopathology 130 (2009) 25-34.
Ferrer-Miralles et al. Microbial factories for recombinant pharmaceuticals, Microbial Cell Factories 2009, 8:17, 1-8.
Grabstein et al. Cloning of a T Cell Growth Factor That Interacts with the beta Chain of the Interleukin-2 Receptor, Science, vol. 264, 1994, 965-968.
Han et al. TGF-beta signaling and its targeting for glioma treatment, Am J Cancer Res 2015, 5(3):945-955.
Hurton, Tethered IL-15 to Augment the Therapeutic Potential of T Cells Expressing Chimeric Antigen Receptor: Maintaining Memory Potential, Persistence, and Antitumor Activity, (2014). UT GSBS Dissertations and Theses (Open Access). 421.
Hurton et al. Tethered IL-15 augments antitumor activity and promotes a stem-cell memory subset in tumor-specific T cells, Proc Natl Acad Sci U S A. 2016,113(48):E7788-E7797.

(Continued)

*Primary Examiner* — Daniel E Kolker
*Assistant Examiner* — Jegatheesan Seharaseyon
(74) *Attorney, Agent, or Firm* — Emory Patent Group

(57) ABSTRACT

This disclosure relates to recombinant proteins comprising a GM-CSF sequence and an interleukin sequence and nucleic acids related thereto. In certain embodiments, the disclosure relates to recombinant proteins comprises N-terminal sequences that are the result of improved production techniques and uses for treating or preventing autoimmune diseases such as multiple sclerosis and cancer.

3 Claims, 6 Drawing Sheets

Specification includes a Sequence Listing.

(56) References Cited

OTHER PUBLICATIONS

Kapust et al. Tobacco etch virus protease: mechanism of autolysis and rational design of stable mutants with wild-type catalytic proficiency, Protein Engineering, 14(12):993-1000, 2001.
Lin et al. Combined immunogene therapy of IL-6 and IL-15 enhances anti-tumor activity through augmented NK cytotoxicity, Cancer Letters 272 (2008) 285-295.
Lucas et al. Dysregulation of IL-15—mediated T-cell homeostasis in TGF-beta dominant-negative receptor transgenic mice, Blood. 2006, 108:2789-2795.
Mortier et al. Soluble Interleukin-15 Receptor alpha (IL-15Ralpha)-sushi as a Selective and Potent Agonist of IL-15 Action through IL-15Rbeta/gamma, J Biol Chem. 2006, 281(3):1612-9.
Ng et al. Activation of NK and CD8+ T-Cells with a Novel IL-15 and TGF-beta Receptor Fusion Protein Confers Anti-Tumor Immunity. Blood, 2015, 126:3421.
Ng et al. Novel TGF-beta antagonist and IL-15 fusion protein enhances formation of memory CD8+ T-cells and prevents the formation of regulatory CD4+ T-cells, Cytotherapy, vol. 17, Issue 6, Supplement, Jun. 2015, p. S19.
Ng et al. Stimulation of natural killer cell-mediated tumor immunity by an IL-15/TGF-beta neutralizing fusion protein, Cancer Res. 2016, 76(19): 5683-5695.
Pennati et al. Maltose-Binding Protein Fusion Allows for High Level Bacterial Expression and Purification of Bioactive Mammalian Cytokine Derivatives, PLoS One 9(9): e106724.
Peti et al. Strategies to maximize heterologous protein expression in *Escherichia coli* with minimal cost, Protein Expression and Purifcation, 51 (2007) 1-10.
Rafei et al. AGMCSF and IL-15 fusokine leads to paradoxical immunosuppression in vivo via asymmetrical JAK/STAT signaling through the IL-15 receptor complex, Blood. 2007,109:2234-2242.
Rafei et al. GIFT15 fusokine to foil immunity's follies, Immunotherapy, 2009, 1(6), 913-15.
Rubinstein et al. Converting IL-15 to a superagonist by binding to soluble IL-15Ralpha, Proc Natl Acad Sci U S A. 2006, 103(24):9166-71.
Sanjabi et al. Opposing effects of TGF-? and IL-15 control the number of short lived effector CD8+ T cells, Immunity. 2009, 31(1): 131-144.
Seay et al. In Vivo Activation of Human NK Cells by Treatment with an Interleukin-15 Superagonist Potently Inhibits Acute In Vivo HIV-1 Infection in Humanized Mice, J Virol, 89:6264-6274, 2015.
Stoklasek et al. Combined IL-15/1L-15Ralpha Immunotherapy Maximizes IL-15 Activity In Vivo, J Immunol. 2006, 177(9): 6072-6080.
Sun et al., Chapter 16, Enhancing the solubility of recombinant proteins in *E. coli* by using hexahistidine-tagged maltose-binding protein as a fusion partner. Methods Mol Biol, 2011, 705, 259-274.
Tagaya et al., Generation of secretable and nonsecretable interleukin 15 isoforms through alternate usage of signal peptides, Proc. Natl. Acad. Sci. USA, vol. 94, pp. 14444-14449, 1997.
Waugh, TEV Protease FAQ, available at http://www.cardiff.ac.uk/biosi/staffinfo/ehrmann/tools/TEVprot.html, 2010.
Zhang et al. Interleukin-15 combined with an anti-CD40 antibody provides enhanced therapeutic efficacy for murine models of colon cancer, Proc Natl Acad Sci U S A. 2009, 106(18):7513-8.

\* cited by examiner

```
            10         20         30         40         50
mGIFT1  --APTRSPITVTRPWKHVEAIKEALNLLDDMPVTLNEEVEVVSNEFSFKKLTCVQTRLKI
        ::::::::::::::::::::::::::::::::::::::::::::::::::::::::::::
rGIFT1  GHAPTRSPITVTRPWKHVEAIKEALNLLDDMPVTLNEEVEVVSNEFSFKKLTCVQTRLKI
            10         20         30         40         50         60

60         70         80         90        100        110
mGIFT1  FEQGLRGNFTKLKGALNMTASYYQTYCPPTPETDCETQVTTYADFIDSLKTFLTDDPGRR
        ::::::::::::::::::::::::::::::::::::::::::::::::::::::::::::
rGIFT1  FEQGLRGNFTKLKGALNMTASYYQTYCPPTPETDCETQVTTYADFIDSLKTFLTDDPGRR
            70         80         90        100        110        120

120        130        140        150        160        170
mGIFT1  AIMKILKPYMRNTSISCYLCFLLNSHFLTEAGIHVFILGCVSVGLPKTEANWIDVRYDLE
        ::::::::::::::::::::::::::::::::::::::::::::::::::::::::::::
rGIFT1  AIMKILKPYMRNTSISCYLCFLLNSHFLTEAGIHVFILGCVSVGLPKTEANWIDVRYDLE
           130        140        150        160        170        180

180        190        200        210        220        230
mGIFT1  KIESLIQSIHIDTTLYTDSDFHPSCKVTAMNCFLLELQVILHEYSNMTLNETVRNVLYLA
        ::::::::::::::::::::::::::::::::::::::::::::::::::::::::::::
rGIFT1  KIESLIQSIHIDTTLYTDSDFHPSCKVTAMNCFLLELQVILHEYSNMTLNETVRNVLYLA
           190        200        210        220        230        240

240        250        260        270        280
mGIFT1  NSTLSSNKNVAESGCKECEELEEKTFTEFLQSFIRIVQMFINTS
        ::::::::::::::::::::::::::::::::::::::::::::
rGIFT1  NSTLSSNKNVAESGCKECEELEEKTFTEFLQSFIRIVQMFINTS
           250        260        270        280
```

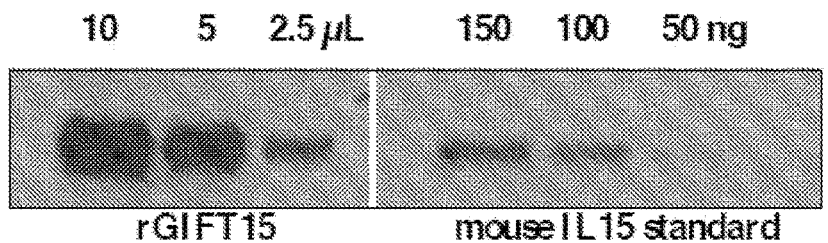

FIG. 5

```
hGIFT1  ---APARSPSPSTQPWEHVNAIQEARRLLNLSRDTAAEMNETVEVISEMPDLQEPTCLQT
           ::::::::::::::::::::::::::::::::::::::::::::::::::::::::
rhGIFT  GRMAPARSPSPSTQPWEHVNAIQEARRLLNLSRDTAAEMNETVEVISEMPDLQEPTCLQT
                 10        20        30        40        50        60

60        70        80        90       100       110
hGIFT1  RLELYKQGLRGSLTKLKGPLTMMASHYKQHCPPTPETSCATQIITFESFKENLKDFLLVG
        ::::::::::::::::::::::::::::::::::::::::::::::::::::::::::::
rhGIFT  RLELYKQGLRGSLTKLKGPLTMMASHYKQHCPPTPETSCATQIITFESFKENLKDFLLVG
                 70        80        90       100       110       120

120       130       140       150       160       170
hGIFT1  SMRISKPHLRSISIQCYLCLLLNSHFLTEAGIHVPILGCFSAGLPKTEANWVNVISDLKK
        ::::::::::::::::::::::::::::::::::::::::::::::::::::::::::::
rhGIFT  SMRISKPHLRSISIQCYLCLLLNSHFLTEAGIHVPILGCFSAGLPKTEANWVNVISDLKK
                130       140       150       160       170       180

180       190       200       210       220       230
hGIFT1  IEDLIQSMHIDATLYTESDVHPSCKVTAMKCFLLELQVISLESGDASIHDTVENLIILAN
        ::::::::::::::::::::::::::::::::::::::::::::::::::::::::::::
rhGIFT  IEDLIQSMHIDATLYTESDVHPSCKVTAMKCFLLELQVISLESGDASIHDTVENLIILAN
                190       200       210       220       230       240

240       250       260       270       280
hGIFT1  NSLSSNGVTESGCKECEELEEKNIKEFLQSFVHIVQMFINTS
        :::::::::::::::::::::::::::::::::::::::::
rhGIFT  NSLSSNGNVTESGCKECEELEEKNIKEFLQSFVHIVQMFINTS
                250       260       270       280
```

FIG. 8

COMPOSITIONS OF GM-CSF AND INTERLEUKIN FUSIONS FOR IMMUNE MODULATION AND USES RELATED THERETO

CROSS-REFERENCE TO RELATED APPLICATIONS

This application is the National Stage of International Application Number PCT/US2015/025514 filed Apr. 13, 2015, which claims the benefit of priority to U.S. Provisional Application No. 61/982,912 filed Apr. 23, 2014. The entirety of each of these applications is hereby incorporated by reference for all purposes.

STATEMENT REGARDING FEDERALLY SPONSORED RESEARCH

This invention was made with government support under Grant 1RO1 A1093881 awarded by the National Institutes of Health. The Government has certain rights in the invention.

BACKGROUND

Current therapies treat symptoms of the autoimmune diseases multiple sclerosis (MS) but there is no cure. Thus, there is a need for improved treatments. An approach to treating autoimmune disorders such as MS and cancer involves the use of cell therapy to alter autoimmune activity of T cells. Under certain conditions manipulated B cells may exert a persistent suppressive effect by provoking the secretion of suppressive factors in the host. Rafei et al., report that a granulocyte-macrophage colony-stimulating factor (GM-CSF) and interleukin-15 (IL-15) fusokine (GIFT15) induces a regulatory B cell population with immune suppressive properties. Nature Medicine, 2009, 15, 1038-1045. See also U.S. Pat. Nos. 7,947,265; 8,647,866; 8,586,055; 8,383,775; 8,013,124; EP 2550359, Grabstein et al., Cloning of a T cell growth factor that interacts with the beta chain of the interleukin-2 receptor, Science, 1994 264 (5161), 965-968; Tagaya et al., Generation of secretable and nonsecretable interleukin 15 isoforms through alternate usage of signal peptides, Proc. Natl. Acad. Sci. U.S.A., 1997, 94 (26), 14444-14449.

Peti & Page report strategies to maximize heterologous protein expression in *Escherichia coli*. Protein Expression Purif. (2007) 51, 1-10.

Sun et al., report enhancing the solubility of recombinant proteins in *E. coli* by using hexahistidine-tagged maltose-binding protein as a fusion partner. Methods Mol Biol, 2011, 705, 259-274

Kapust et al., report tobacco etch virus proteases mechanism of autolysis and design of stable mutants. Protein Eng., 2001, 14:993-1000.

References cited herein are not an admission of prior art.

SUMMARY

This disclosure relates to recombinant proteins comprising a GM-CSF sequence and an interleukin sequence and nucleic acids related thereto. In certain embodiments, the disclosure relates to recombinant proteins comprising N-terminal sequences that are the result of improved production techniques and uses for treating or preventing autoimmune diseases such as MS and cancer In certain embodiments, the disclosure relates to recombinant proteins comprising a) an N-terminal sequence selected from glycine-histidine amino acid sequence or an N-terminal serine-histidine amino acid sequence; b) a human GM-CSF sequence; and c) a human interleukin sequence.

In certain embodiments, the human interleukin sequence is IL-2, IL-4, IL-9, or IL-15.

In certain embodiments, the recombinant protein is not glycosylated.

In certain embodiments, the disclosure relates to recombinant proteins that are not glycosylated comprising a human GM-CSF sequence and a human interleukin 15 sequence produced by expression in bacteria.

In certain embodiments, the disclosure relates to a recombinant protein comprising or consisting of GHMAPARS$^{11}$PS$^{12}$ PS$^{13}$ T$^{14}$ QPWEHVNAIQEARRLLN$^{15}$ LSRDTAEMN$^{16}$ ETVEVISEMFDLQEP TCLQTRLELYKQGLRGSLTKLKGPLTMMASHYKQHCPPTPETSCATQIITFESFKENLKDFLLVGSMRISKPHLRSISIQCYLCLLLNSHFLTEAGIHVFILGCFSAGLPKTEANWVNVISDLKKIEDLIQSMHIDATLYTESDVHPSCKVTAMKCFLLEL-QVISLESGDASIHDTVENLIILANNSLSSNGN$^{17}$V-TESGCKECEELEEKNIKEFLQSFVHIVQMFINTS (SEQ ID NO: 12) wherein S$^{11}$, S$^{12}$, S$^{13}$, T$^{14}$, N$^{15}$, N$^{16}$, and N$^{17}$ are not conjugated to a glycan. In certain embodiments, variants of SEQ ID NO: 12 are contemplated such as when one or two of the amino acids are deleted. In certain embodiments, the disclosure contemplates that M at the N-terminal position 3 may be deleted. In certain embodiments, also contemplated are variants wherein the linker S between the GM-CSF sequence and IL15 sequence is made longer e.g., by one or two amino acids, such as a SGG linker or an SGS linker—longer linkers are also contemplated provided the recombinant proteins retains functional characteristics.

In certain embodiments, the disclosure relates to recombinant nucleic acids that encode recombinant proteins disclosed herein. In certain embodiments, the disclosure relates to protein expression systems comprising recombinant nucleic acids disclosed herein. In certain embodiments, the disclosure relates to recombinant proteins disclosed herein expressed in a prokaryotic cell. In certain embodiments, the prokaryotic cell is a genetically modified *E. coli*. In certain embodiments, the disclosure relates to recombinant proteins disclosed herein expressed in a yeast cell.

In certain embodiment, the disclosure relates to recombinant proteins made by the process of expressing a pre-cleavage recombinant protein in a prokaryotic cell, wherein the pre-cleavage recombinant protein comprises a cleavage sequence E-X$^{18}$-X$^{19}$-Y-X$^{20}$-Q-X$^{21}$-H (SEQ ID NO: 13), wherein X$^{18}$, X$^{19}$, and X$^{20}$ are independently any amino acid, and X$^{21}$ is G or S, and mixing the pre-cleavage recombinant protein with a tobacco etch virus (TEV) protease under conditions such that a recombinant protein with an N-terminal comprising X$^{21}$-H— is formed. In certain embodiment, the cleavage sequence is ENLYFQGH (SEQ ID NO: 14). In certain embodiments, the pre-cleavage recombinant protein further comprises a maltose-binding protein.

BRIEF DESCRIPTION OF THE FIGURES

FIG. 5 shows sequences and data on western blot analysis of purified rGIFT15 and IL-15. Immunodetection was conducted with anti-mouse IL-15 antibody. mGIFT15 is eukaryotic derived murine GIFT15 (SEQ ID NO: 20) and murine rGIFT15 is bacterial (recombinant) GIFT15 (SEQ ID NO: 21). Highlighted are residues glycosylated in the mammalian form of GIFT15. Note the first two amino acids of the recombinant form of GIFT15 missing in the eukaryotic GIFT15.

FIG. 8 shows sequences for human recombinant GIFT15. hGIFT15 is eukaryotic derived GIFT15 (SEQ ID NO: 22), rhGIFT15 is bacterial (recombinant) GIFT15 (SEQ ID NO: 12). Highlighted are residues glycosylated in the mammalian form of GIFT15. Note the first three amino acids of the bacterial recombinant form of GIFT15 missing in the eukaryotic GIFT15.

DETAILED DISCUSSION

Figure 1:
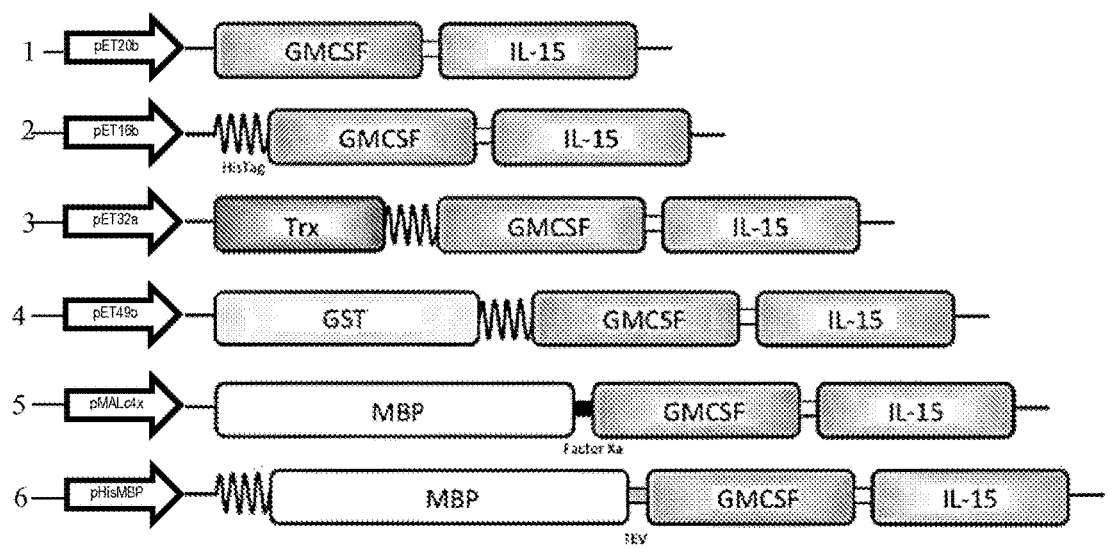
FIG. 1 shows a schematic representation of the plasmid vector constructs tested for expression of mouse GIFT15 in *E. coli*. 1. pET20b: expression of GIFT15 without any tag, GM-CSF domain (lacking the signal peptide, green box) and IL-15 domain (blue box). The linker between the two domains is formed from the signal peptide and propeptide of IL-15 (grey box). 2. pET16b: expression of GIFT15 with an additional His-tag (6×-His) at the N-terminus of the fusokine. 3. pET32b: expression of GIFT15 downstream of thioredoxin (TRX, red box) followed by a His-tag. 4. pET42b: expression of GIFT15 in fusion with glutathione S-transferase (GST, yellow box). 5. pMALc4x: expression of GIFT15 in fusion with the maltose-binding protein (MBP, white box). 6. pHisMBP: expression of GIFT15 with the addition of a His-tag at the N-terminus of the MBP domain and replacement of the Factor Xa protease recognition site with that of the TEV protease.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Terms

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

The terms "protein" and "polypeptide" refer to compounds comprising amino acids joined via peptide bonds and are used interchangeably.

The term "glycan" refers to saccharides and polysaccharides typically conjugated to proteins produced in eukaryotic cells.

In certain embodiments, the disclosure contemplates that any of the polypeptide sequences may be variants having greater than 90 or 95% identity or similarity. The term "variant" when used in reference to a polypeptide refers to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

In certain embodiments, the disclosure relates to a polypeptide having any of the sequences disclosed or variants thereof having a C-terminal modification such as an amide, substituted amide, N-alkylamide, polyethylene glycol amide, ester, substituted ester, O-alkylester, polyethylglycol ester, thioester, substituted thioester, N-alkylthio ester, polyethylene glycol thiol ester, or derivative thereof e.g., polypeptide(C=O)—NH$_2$, polypeptide(C=O)—NHalkyl, polypeptide(C=O)—NH-PEG, polypeptide(C=O)—Oalkyl, polypeptide(C=O)—Oalkyl, polypeptide(C=O)—O-PEG, polypeptide(C=O)—SH, polypeptide(C=O)—Salkyl, polypeptide(C=O)—S-PEG. In certain embodiments, the disclosure relates to a polypeptide having any of the sequences disclosed having an N-terminal modification such as a substituted amine, alkylamino, alkanoyl, substituted alkanoyl.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxy group. Contemplated derivative include switching carbocyclic, aromatic or phenyl rings with heterocyclic rings or switching heterocyclic rings with carbocyclic, aromatic or phenyl rings, typically of the same ring size. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze, all hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxy, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkylamino" refers an alkyl group as defined above attached through an amino bridge. An example of an alkylamino is methylamino, (i.e., —NH—$CH_3$).

"Alkanoyl" refers to an alkyl as defined above attached through a carbonyl bridge (i.e., —(C═O)alkyl).

As used herein, the term "combination with" when used to describe administration with an additional treatment means that the agent may be administered prior to, together with, or after the additional treatment, or a combination thereof.

The term "nucleic acid" refers to a polymer of nucleotides, or a polynucleotide. The term is used to designate a single molecule, or a collection of molecules. Nucleic acids may be single stranded or double stranded, and may include coding regions and regions of various control elements, as described below.

The term "a nucleic acid sequence encoding" a specified polypeptide refers to a nucleic acid sequence comprising the coding region of a gene or in other words the nucleic acid sequence which encodes a gene product. The coding region may be present in either cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

Human GM-CSF and Interleukin Sequences

In certain embodiments, the disclosure relates to recombinant proteins comprising N-terminal sequences that are the result of improved production techniques. In certain embodiments, the disclosure relates to recombinant proteins comprising a) an N-terminal sequence selected from glycine-histidine amino acid sequence or an N-terminal serine-histidine amino acid sequence; b) a human GM-CSF sequence; and c) a human interleukin sequence.

In certain embodiments, the disclosure relates to recombinant proteins comprising a) an N-terminal sequence selected from glutamic acid-alanine amino acid sequence; b) a human GM-CSF sequence; and c) a human interleukin sequence.

In certain embodiments, the human GM-CSF sequence comprises AP $X^1$ RSPSPSTQPWEHVNAIQEARRLLNLSRDTAAEMNETVEVISEMFDLQEPTCLQTRLELYKQGLRGSLTKLKGPLT $X^2$ MASHYKQHCPPTPETSCATQ $X^3$ ITFES $X^4$ KENLKDFLLV (SEQ ID NO: 1), wherein $X^1$ is A or G, $X^2$ is M or K, $X^3$ is I or T, $X^4$ is F or L; or variants or fragments thereof, wherein fragments are greater than 50, 100, or 150 amino acids.

In certain embodiments the human GM-CSF sequence comprises APARSPSPSTQPWEHVNAIQEARRLLNLSRDTAAEMNETVEVISEMFDLQEPTCLQTRLELYKQGLRGSLTKLKGPLTMMASHYKQHCPPTPETSCATQIITFESFKENLKDFLLV (SEQ ID NO: 2); APA RSPSPSTQPW EHVNAIQEAR RLLNLSRDTA AEMNETVEVI SEMFDLQEPT CLQTRLELYK QGLRGSLTKL KGPLTMMASH YKQHCPPTPE TSCATQTITF ESFKENLKDF LLV (SEQ ID NO: 3); APG RSPSPSTQPW EHVNAIQEAR RLLNLSRDTA AEMNETVEVI SEMFDLQEPT CLQTRLELYK QGLRGSLTKL KGPLTMMASH YKQHCPPTPE TSCATQTITF ESFKENLKDF LLV (SEQ ID NO: 4), or APARSPSPSTQPWEHVNAIQEARRLL NLSRDTAAE MNETVEVISEMFDLQEPTCLQTRLELYKQGLRGSLTKLKGPLTMMASHYKQHCPPT PETSCAT QIITFESFKENLKDFLLVIPFDCWEPVQE (SEQ ID NO: 26) or variants or fragments thereof, wherein fragments are greater than 50, 100, or 150 amino acids.

In certain embodiments, the human GM-CSF sequence comprises APARS[11] PS[12] PS[13] T[14] QPWEHVNAIQEARRLLN[15] LSRDTAAEMN[16] ETVEVISEMFDLQEPTCLQTRLELYKQGLRGSLTKLKGPLTMMASHYKQHCPPTPETSCATQIITFESFKENLKDFLLV (SEQ ID NO: 2) and the IL-15 sequence comprises RISKPHLRSISIQCYLCLLLNSHFLTEAGIH VFILG CFSAGLPKTE ANWVNVISDL KKIEDLIQSM HIDATLYTES DVHPSCKVTA MKCFLLELQV ISLESGDASI HDTVENLIIL ANNSLSSNGN[17] VTESGCKECE ELEEKNIKEF LQSFVHIVQM FINTS (SEQ ID NO: 11) or variants or fragments thereof, wherein fragments are greater than 50, 100, or 150 amino acids.

In certain embodiments, one or more of $S^{11}$, $S^{12}$, $S^{13}$, $T^{14}$, $N^{15}$, $N^{16}$, and $N^{17}$ are not conjugated to a glycan.

In certain embodiments, the human interleukin sequence is IL-2, IL-4, IL-9, or IL-15.

In certain embodiments, the human IL-15 sequence comprises NWVNVISDLKKIEDLIQSMHIDATLYTESDVHP-SCKVTAMKCFLLELQVISLESGDASIHDTVENLIILA-NNSLSSNGNVTESGCKECEELE $X^5$ KNIKEFLQSFV-HIVQMFINTS (SEQ ID NO: 5) wherein $X^5$ is E or K; or variants or fragments thereof, wherein fragments are greater than 50, 100, or 150 amino acids.

In certain embodiments, the human IL-15 sequence comprises $X^6$ $X^7$ $X^8$ $X^9$ $X^{10}$ CFSAGLPKTE ANWVNVISDL KKIEDLIQSM HIDATLYTES DVHPSCKVTA MKCFL-LELQV ISLESGDASI HDTVENLIIL ANNSLSSNGN VTESGCKECE ELE $X^5$ KNIKEF LQSFVHIVQM FIN (SEQ ID NO: 6) wherein $X^6$ is L, I, or V; $X^7$ is F or D; $X^8$ is L, I, or V; $X^9$ is L or C; $X^{10}$ is G or S; and $X^5$ is E or K or variants or fragments thereof, wherein fragments are greater than 50, 100, or 150 amino acids.

In certain embodiments, $X^6$ $X^7$ $X^8$ $X^9$ $X^{10}$ is the sequence VFILG (SEQ ID NO: 7) or IDLCS (SEQ ID NO: 8).

In certain embodiments, the human IL-15 sequence comprises VLGT IDLCS CFSAGLPKTE ANWVNVISDL KKIEDLIQSM HIDATLYTES DVHPSCKVTA MKCFL-LELQV ISLESGDASI HDTVENLIIL ANNSLSSNGN VTESGCKECE ELEEKNIKEF LQSFVHIVQM FINTS (SEQ ID NO: 9); VLGT IDLCS CFSAGLPKTE ANWVN-VISDL KKIEDLIQSM HIDATLYTES DVHPSCKVTA MKCFLLELQV ISLESGDASI HDTVENLIIL ANNSL-SSNGN VTESGCKECE ELEKKNIKEF LQSFVHIVQM FINTS (SEQ ID NO: 10); RISKPHLRSISIQCYLCLLLN-SHFLTEAGIH VFILG CFSAGLPKTE ANWVNVISDL KK IEDLIQSM HIDATLYTES DVHPSCKVTA MKCFL-LELQV ISLESGDASI HDTVENLIIL AN NSLSSNGN VTESGCKECE ELEEKNIKEF LQSFVHIVQM FINTS (SEQ ID NO: 11), or variants or fragments thereof, wherein fragments are greater than 50, 100, or 150 amino acids.

In certain embodiments, the IL-2 sequence is APTSSST-KKT QLQLEHLLLD LQMILNGINN YKNPKLTRML TFKFYMPKKA TELKHLQCLE EELKPLEEVL NLAQ-SKNFHL RPRDLISNIN VIVLELKGSE TTFMCEYADE TATIVEFLNR WITFCQSIIS (SEQ ID NO: 15) or variants or fragments thereof, wherein fragments are greater than 50 or 100 amino acids.

In certain embodiments, the IL-4 sequence is GLTSQLLPP LFFLLACAGN FVHGHKCDIT LQEIIK-TLNS LTEQKTLCTE LTVTDIFAAS KNTTEKETFC RAATVLRQFY SHHEKDTRCL GATAQQFHRH KQLIR-FLKRL DRNLWGLAGL NSCPVKEANQ STLENFLERL KTIMREKYSK CSS (SEQ ID NO: 16); FVHGHKCDIT LQEIIKTLNS LTEQKTLCTE LTVTDIFAAS KNTTEKE-TFC RAATVLRQFY SHHEKDTRCL GATAQQFHRH KQLIRFLKRL DRNLWGLAGL NSCPVKEANQ STLEN-FLERL KTIMREKYSK CSS (SEQ ID NO: 27); or LQEIIKTLNS LTEQKTLCTE LTVTDIFAAS KNT-TEKETFC RAATVLRQFY SHHEKDTRCL GATAQQF-HRH KQLIRFLKRL DRNLWGLAGL NSCPVKEANQ STLENFLERL KTIMREKYSK CSS (SEQ ID NO: 28) or variants or fragments thereof, wherein fragments are greater than 50, 100, or 150 amino acids.

In certain embodiments, the IL-9 sequence is VLT-SALLLCSVAGQGCPTLAGILDINFLINKMQEDPASK-CHCSANVTSCLCLGIPSDNCTRPCFSERLSQMTNTT-MQTRYPLIFSRVKKSVEVLKNNKCPYFSCEQPCNQT-TAGNALTFLKSLLEIFQKEKMRGMRGKI (SEQ ID NO: 17) or MLLAMVLTSALLL CSVAGQGCPTLAGILDINF-LIN KMQ EDPASKCHCS ANVTSCLCLGIPSDNCTRP-CFSERLSQMT NTTMQTR YPLIFSRVKK SVEVLK NNKCPYFSCEQPCNQTTAGNALTFLKSLLEIFQKEK-MRGMRGKI (SEQ ID NO: 29) variants or fragments thereof, wherein fragments are greater than 50 or 100 amino acids.

Maltose-Binding Protein Tag Allows for High Level Bacterial Expression and Purification of Bioactive Mammalian Cytokine Derivatives The physical coupling of cytokines in a single polypeptide results in synergistic bioactivity not observed by the use of parent cytokines. For example, fusion of GM-CSF with γ chain interleukins such as IL-2, IL-4, IL-9, IL-15 and IL-21 as a chimeric protein typically leads to gain-of-function properties when compared to the bioactivity of GM-CSF and the interleukins individually. Certain GIFTs (GM-CSF and Interleukin Fusion Transgenes) result in STAT hyperphosphorylation in responding lymphomyeloid cells.

Figure 9:
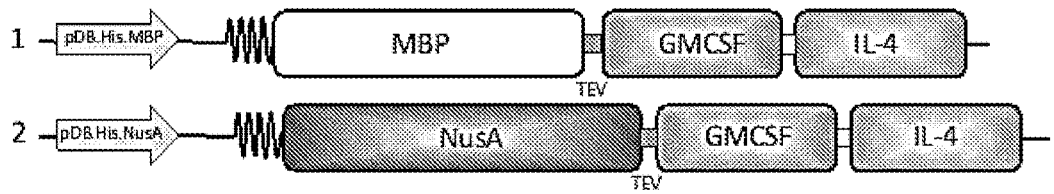
FIG. 9 shows a schematic representation of the plasmid vector constructs tested for expression of mouse/human GIFT4 in *E. coli*. 1. pDB.His.MBP: expression of GIFT4 with the addition of a His-tag at the N-terminus of the MBP domain and TEV protease recognition site. 2. pDB.His.NusA: expression of GIFT4/GIFT15 with the addition of a His-tag at the N-terminus of the NusA domain and TEV protease recognition site.

Human GIFT4 was express with bacterial fermentation. Mouse and human GIFT4 were subcloned in 2 different vectors that combine the expression of GIFT4 with maltose-binding protein (MBP, vector 1 in FIG. 1) or N utilization substance A (NusA, vector 2 in FIG. 9). Expression of recombinant GIFT4 was optimized, for both the murine and human version, by varying bacterial growth and induction conditions. Bacterial colonies, transformed with the two expression vectors. Preliminary result suggested that only pDB.His.NusA was able to allow the accumulation of recombinant mouse/human GIFT4 in the intracellular milieu as confirmed by western blotting for human GIFT4 by using antibody anti human GM-CSF. The protein has been purified on Nickel chelate chromatography in FPLC and digested with TEV protease. After removal of the NusA tag and endotoxin the protein has been gel-filtered in PBS buffer and test for bioactivity. No activity was detected for either murine or human sequences GIFT4 produced in *E. coli*.

GIFT15 binds atypically to the trimeric IL-15 receptor. As a result, asymmetrical signaling takes place downstream of the IL-15 receptor, leading to the hyperactivation of STAT3 and suppression of γ chain-mediated STAT5 phosphorylation. This co-opting of IL-15R singling machinery leads to an unusual cell physiological response, chiefly the ability of GIFT15 to reprogram naïve B cells into regulatory CD1d+/CD5+ B cells that secrete IL-10. Ex vivo GIFT15-derived regulatory B cells with immunosuppressive properties is an attractive prospective autologous cell therapy for autoimmune diseases such as multiple sclerosis.

An improved manufacturing approach was needed. An efficient method to produce an improved recombinant GM-CSF and IL-15 chimeric polypeptide, GIFT15, in *E. coli* is provided. Expression of a maltose-binding protein (MBP) fusion protein efficiently allowed the accumulation of soluble protein in the intracellular milieu. Optimizing the bacterial culture significantly increased the yield of recombinant protein. This approach led to the production of soluble, endotoxin-free functional protein, averaging 0.5 mg of rGIFT15 per liter of culture.

Recombinant proteins produced in *E. coli* lack certain post-translational modifications which are present in many eukaryotic produced proteins. Glycosylation is the most common post-translational modification in eukaryotic cells. Because GIFT15 is highly glycosylated, it was uncertain as to whether GIFT15 produce in *E. coli* would produce a viable product as previously reported for other bacterial derived proteins (Magné N. et al., Impact of glycosylation on the effect of cytokines. A special focus on oncology. Eur Cytokine Netw., (2002); 13(2):154-60. Tsuda E. et al., The role of carbohydrate in recombinant human erythropoietin. *Eur. J. Biochem.*, (1990) 188: 405. Mancilla J., et al., Importance of glycosylation for receptor binding and biological activity of IL-6. *Molecular and Cellular Biology of cytokines*, Wiley-Liss, (1990), 51-56. Karpusas M. et al., The structure of human interferon beta: implications for activity. (1988) *Cell. Mol. Life Sci.* 54: 1203.)

A method was developed to generate and purify bacterial-derived GIFT15 (rGIFT15). Bacterial-derived GIFT15 maintains potent bioactivity despite the absence of any eukaryotic post-translational modification.

Heterologous expression in *E. coli* was selected. Five constructs were tested in order to achieve high-level soluble expression of the recombinant protein. The GIFT15 fusokine made by this method was unstable in the *E. coli* cytoplasm. Only trace amounts were detectable by Western blot analysis when no tag was used or when a His-tag was added at the N-terminal of the protein. A cause of the observed instability was unknown, one possibility is that an aberrant tertiary structure resulted due to improper disulfide bridge structures within GIFT15. Indeed, disulfide bonds can be important stabilizing structures for proteins, but the reducing environment of *E. coli* cytoplasm can be a challenge for the proper folding of recombinant proteins, leading to their accumulation within inclusion bodies. Alternatively, misfolded proteins are quickly proteolyzed from the intracellular milieu. GIFT15 has 3 disulfide bonds, one of which is in the GM-CSF domain and the other two are in the IL-15 domain.

To facilitate the formation of disulfide bounds, GIFT15 was fused with thioredoxin. The GIFT15-thioredoxin fusion was more abundantly expressed and protected GIFT15 from degradation. Unfortunately thioredoxin did not improve the solubility of the complete recombinant fusokine, as it also accumulated in inclusion bodies. Similar results were obtained when GIFT15 was fused with glutathione S-transferase.

An optimized strategy in which abundant expression of GIFT15 was observed as a soluble protein was the addition of MBP at the N-terminal of GIFT15. In initial attempts to purify the fusion protein, mouse GIFT15 was isolated with the use of a MBP-binding amylose column, followed by treatment with Factor Xa protease to cleave the MBP carrier. Anion exchange chromatography using DEAE-Sepharose was able to remove the recombinant GIFT15 from the protease. Unfortunately, most of the protein was lost in the flow-through of the amylose column. Moreover, non-specific cleavage of the fusion protein by Factor Xa was observed. To address these issues, MBP was used as a protein stabilizer and a His-tag was added to allow for selectivity as part of a metal-chelate chromatography purification scheme. In addition, substituting the Factor Xa cleavage site with that for the TEV protease allowed for efficient removal of tags without non-specific proteolytic degradation of the GIFT15 polypeptide sequence.

Stimulation of unfractionated mouse splenocytes or purified B cells with GIFT15 induced asymmetrical signaling on responsive lymphomyeloid cells downstream of the IL-15 receptor, causing STAT3 hyperphosphorylation and STAT5 hypophosphorylation. Following tyrosine phosphorylation, STAT3 proteins dimerize, translocate to the nucleus, and activate specific target genes. Accordingly, STAT3 activation is associated with cell growth, anti-apoptosis, and pro-survival properties. Furthermore, GIFT15-stimulated Bregs expressed surface molecules that are typical markers within a panel of inducible Bregs. Flow cytometry profiles of GIFT15-induced Bregs revealed their phenotype as CD1d, CD21, CD22, CD23, CD24, CD138, IgM, IgD and MHCII positive cells. These specific markers identify a subset of Bregs whose regulatory function is mediated by the production of IL-10 as confirmed by detecting the release of IL-10 in the media of stimulated B cells.

Fusokines can be manufactured utilizing eukaryotic cell expression systems with downstream processing and protein purification. More efficient and productive protein expression systems include those derived from bacteria (i.e. *Escherichia coli*) and yeast (i.e. *Pichia pastoris*).

Bacterial expression systems are suitable for production of recombinant proteins. Recombinant proteins produced in *E. coli* nonetheless lack certain post-translational modifications which are present in many eukaryotic proteins. Glycosylation is the most common post-translational modification. GM-CSF, IL-4 and IL-15 are glycosylated. Although the absence of bacterial N- or O-glycans can limit the therapeutic potential of bacteria-derived leukines, several cytokine products have now been tested in the clinic and in certain cases the absence of glycans does not affect the biological activity of the recombinant protein.

Alternatively, in order to overcome the limitation of absence post-translational modifications, murine and human GIFT4/human GIFT15 were expressed in the methylotrophic yeast, *P. pastoris*. The expressed proteins can undergo secretion pathway and be subjected to post-translational modifications. Foreign genes are expressed under the control of the tightly regulated methanol-induced alcohol oxidase 1 promoter.

Methods of Use

In certain embodiments, the disclosure relates to methods of treating or preventing an immune response comprising, isolating B-cells from a subject; mixing the B-cells with a GIFT15 disclosed herein under conditions such that modified cells are formed, wherein the modified cells express major histocompatibility complex class I (MHCI), MHCII, and secrete IL-10; and administering an effect amount of the modified cells to the subject in need thereof. In certain embodiments, the immune response is an autoimmune disease, rejection of transplanted cell, tissue, or organ, or allergic response. In certain embodiments, the autoimmune disease is selected from multiple sclerosis, rheumatoid arthritis, ulcerative colitis, Crohn's disease, Lupus erythematosus, and diabetes mellitus type 1. In certain embodiments the autoimmune disease is sarcoidosis, focal segmental glomerulosclerosis, Behcet's Disease, or pemphigus.

In certain embodiments, the method further comprises the step of co administration of an immunosuppressive agent and/or anti-inflammatory agent to the subject. In certain embodiments, the subject is diagnosed with multiple sclerosis and the above methods are performed in combination with administering interferon-beta (IFN-beta), glatiramer acetate, mitoxantrone, natalizumab, or combinations thereof.

In certain embodiments, the immunosuppressive agent is cortisol (hydrocortisone), cortisone, prednisone, prednisolone, methylprednisolone, dexamethasone, betamethasone, triamcinolone, beclometasone, fludrocortisone, deoxycorticosterone, aldosterone, methotrexate, azathioprine, mercaptopurine, dactinomycin, muromonab-CD3, basiliximab, daclizumab, ciclosporin, tacrolimus, sirolimus, infliximab, etanercept, adalimumab, belatacept, or abatacept.

In certain embodiments, the anti-inflammatory agent is acetylsalicylic acid, diflunisal, salsalate, choline magnesium trisalicylate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, aceclofenac, piroxicam, meloxicam, tenoxicam, droxicam, lornoxicam, isoxicam, mefenamic acid, meclofenamic acid, flufenamic acid, tolfenamic acid, etoricoxib, or licofelone.

In certain embodiments, isolating B cells from a subject may be performed by any variety of methods. B cells mature after they exit the bone marrow where they are produced. Newly formed surface IgM$^+$ B cells in the bone marrow are immature. Mature B cells typically yield two subsets of mature B cells called follicular and marginal zone B cells. Peripheral blood typically contains follicular B cells. These are the cells that cooperate with T cells to generate the adaptive immune responses. Noncirculating mature B cells are typically found into the marginal zone (MZ) of the spleen. Marginal zone B cells differentiate into plasma cells independent of T cell help. Transitional B cells are those in stages before maturation.

The B cell receptor (BCR) directly interacts with antigens. CD19 expression occurs in the early stages of B cell development and acts downstream of BCR signaling. The marginal zone B cells typically express high levels of IgM, CD21, CD1, CD9 with low to negligible levels of IgD, CD23, CD5, and CD11b that help to distinguish them phenotypically from follicular B cells.

In certain embodiments, the disclosure contemplates isolating B cells from the spleen by removing all or a portion of the spleen from a subject, e.g., human subject, disrupting, and extracting the B cells into an salt solution optionally containing nutrients, saccharides, or other cell nutrients, e.g., phosphate-buffered saline or Hank's balanced salt solution, followed by centrifugation and separation of the cells. In certain embodiments, B cell purification is done by positive selection according to lineage markers or by depletion of non-B cells using fluorescence activated cell sorting or magnetic beads that specifically bind surface markers.

In certain embodiments, CD19 expressing cells can be isolated from different cell sources such as human peripheral blood mononucleated cells (PBMCs), bone marrow, lymphoid tissues, or cell cultures. PBMCs can be extracted from whole blood using ficoll, a hydrophilic polysaccharide that separates layers of blood, which will separate the blood into a top layer of plasma, followed by a layer of PBMCs and a bottom fraction of polymorphonuclear cells.

In certain embodiments, the GM-CSF and IL (GIFT) conjugates of the disclosure, or produced by methods disclosed herein, may be employed in methods for treating or preventing a variety of diseases and pathologic conditions, including genetic diseases, congenital diseases and acquired diseases such as infectious diseases (e.g. viral and/or bacterial infections), cancer, immune deficiency diseases, and autoimmune diseases. Accordingly, the present disclosure also encompasses the use of the fusion protein, vector, infectious viral particle, host cell or composition of the disclosure for the preparation of a drug intended for treating or preventing such diseases, and especially cancer or an infectious disease.

The composition of the present disclosure is particularly intended for the preventive or curative treatment of disorders, conditions or diseases associated with cancer. The term "cancer" encompasses any cancerous conditions including diffuse or localized tumors, metastasis, cancerous polyps and preoplastic lesions (e.g. dysplasias) as well as diseases which result from unwanted cell proliferation. A variety of tumors may be selected for treatment in accordance with the methods described herein. In general, solid tumors are typical. Cancers which are contemplated in the context of the disclosure include without limitation glioblastoma, sarcoma, melanomas, mastocytoma, carcinomas as well as breast cancer, prostate cancer, testicular cancer, ovarian cancer, endometrial cancer, cervical cancer (in particular, those induced by a papilloma virus), lung cancer (e.g. lung carcinomas including large cell, small cell, squamous and adeno-carcinomas), renal cancer, bladder cancer, liver cancer, colon cancer, anal cancer, pancreatic cancer, stomach cancer, gastrointestinal cancer, cancer of the oral cavity, larynx cancer, brain and CNS cancer, skin cancer (e.g. melanoma and non-melanoma), blood cancer (lymphomas, leukemia, especially if they have developed in solid mass), bone cancer, retinoblastoma and thyroid cancer. In one typical embodiment of the use of the disclosure, the composition is administered into or in close proximity to a solid tumor.

In certain embodiments, the disclosure contemplates uses of conjugates disclosed herein in autologous immune enhancement therapy (AIET). AIET is a treatment method in which immune or cancer cells, e.g., lymphokine-activated killer (LAK) cells, natural killer (NK) cells, cytotoxic T lymphocytes (CTLs), dendritic cells (DCs), are taken out from the body of a subject which are cultured and processed to activate them until their resistance to cancer is strengthened and then the cells are put back in the body. The cells, antibodies, and organs of the immune system work to protect and defend the body against the tumor cells. In certain embodiments, the disclosure contemplates mixing harvested cells with a GIFT disclosed herein, e.g., conjugates of GM-CSF and IL-4 to activate them. In certain embodiments, the disclosure contemplates administering conjugates of GM-CSF and IL-4 when the cells are administered back to the subject.

In certain embodiments, the disclosure contemplates the administration of sipuleucel-T (PROVENGE) in combination with a GIFT disclosed herein, e.g., conjugate of GM-CSF and IL-4. PROVENGE consists of autologous peripheral blood mononuclear cells, including antigen presenting cells (APCs), that have been activated during a culture period with a recombinant human protein, PAP-GM-CSF, consisting of prostatic acid phosphatase (PAP), an antigen expressed in prostate cancer tissue, linked to GM-CSF. In certain embodiments, the disclosure relates to a conjugate comprising PAP, GM-CSF, and IL-4, and uses in activating antigen presenting cells in peripheral blood mononuclear cells. The peripheral blood mononuclear cells of the subject may be obtained via a standard leukapheresis procedure prior to infusion. During culture, the recombinant antigen can bind to and be processed by antigen presenting cells (APCs). The recombinant antigen is believed to direct the immune response to PAP. The infused product is believed to contain antigen presenting cells, dendritic cells, T cells, B cells, natural killer (NK) cells, and other cells. Typically each dose contains more than 50 million autologous CD54$^+$ cells activated with PAP-GM-CSF or PAP-GM-CSF-IL-4. The potency is typically evaluated by measuring the increased expression of the CD54 molecule, also known as ICAM-1, on the surface of APCs after culture with PAP-GM-CSF or PAP-CM-CSF-IL-4. CD54 is a cell surface molecule that plays a role in the immunologic interactions between APCs and T cells, and is considered a marker of immune cell activation.

In certain embodiments, the disclosure contemplates methods for treating cancer comprising administering a GIFT disclosed herein, e.g., GM-CSF and IL-4 conjugate disclosed herein, as an immune adjuvant in combination with a vector that encodes a tumor associated antigen/cancer marker, such as PSA, PAP, and optionally encoding other co-stimulatory molecules selected from, B7-1, B7-2, ICAM-1, GM-CSF, leukocyte function-associated antigen-3 (LFA-3). Other embodiments contemplated for the treatment of cancer include administering an effective amount of a vector that encodes a GM-CSF and IL-4 conjugate disclosed herein and optionally further encodes a tumor associated antigen/cancer marker and optionally encodes other co-stimulatory molecules to a subject. PROSTVAC is a recombinant vector encoding costimulatory molecules, as well as PSA as a vaccine target. Plasmid DNA is incorporated into either vaccinia or fowlpox viruses by means of a packing cell line. Patients are treated with a vaccinia prime followed by a series of fowlpox-based boosts.

In certain embodiments, the disclosure relates to methods of treating cancer comprising administering a GIFT disclosed herein, e.g., GM-CSF and IL-4 conjugate, in combination with an anti-CTLA-4 antibody. Anti-CTLA-4 antibody is contemplated to be administered in combination with any of the methods disclosed herein. It is believed that it binds to CTLA-4 surface glycoprotein on T-cell surface, minimizing immune autoregulation and potentially enhancing antitumor activity. Interactions between B7 molecules on antigen-presenting cells and CTLA-4 on tumor-specific T cells are inhibitory. Thus, CTLA-4 engagement negatively regulates the proliferation and function of such T cells. Under certain conditions, blocking CTLA-4 with a monoclonal antibody (ipilimumab or tremilimumab) restores T-cell function.

Other embodiments contemplated for the treatment of cancer include methods that utilize the extraction of cancer cells from a subject and incorporate glycosyl-phosphatidylinositol (GPI)-anchored co-stimulatory molecules such as B7-1 and B7-2 into tumor cell membranes optionally with a conjugate GM-CSF and IL-4 anchored GPI, and administering the modified cells to the subject in combination with a conjugate of GM-CSF and IL-7 to elicit an immune response. See e.g., McHugh et al., Cancer Res., 1999, 59(10):2433-7; Poloso et al., Mol Immunol., 2002, 38(11): 803-16; and Nagarajan & Selvaraj, Cancer Res., 2002, 62(10):2869-74.

Other pathologic diseases and conditions are also contemplated in the context of the disclosure, especially infectious diseases associated with an infection by a pathogen such as fungi, bacteria, protozoa and viruses. Representative examples of viral pathogens include without limitation human immunodeficiency virus (e.g. HIV-1 or HIV-2), human herpes viruses (e.g. HSV1 or HSV2), cytomegalovirus, Rotavirus, Epstein Barr virus (EBV), hepatitis virus (e.g. hepatitis B virus, hepatitis A virus, hepatitis C virus and hepatitis E virus), varicella-zoster virus (VZV), paramyxoviruses, coronaviruses; respiratory syncytial virus, parainfluenza virus, measles virus, mumps virus, flaviviruses (e.g. Yellow Fever Virus, Dengue Virus, Tick-borne encephalitis virus, Japanese Encephalitis Virus), influenza virus, and typically human papilloma viruses (e.g. HPV-6, 11, 16, 18, 31. 33). Representative examples of bacterial pathogens include *Neisseria* (e.g. *N. gonorrhea* and *N. meningitidis*); *Bordetella* (e.g. *B. pertussis, B. parapertussis* and *B. bronchiseptica*), *Mycobacteria* (e.g. *M. tuberculosis, M. bovis, M. leprae, M. avium, M. paratuberculosis, M. smegmatis*); *Legionella* (e.g. *L. pneumophila*); *Escherichia* (e.g. enterotoxic *E. coli*, enterohemorragic *E. coli*, enteropathogenic *E. coli*); *Vibrio* (e.g. *V. cholera*); *Shigella* (e.g. *S. sonnei, S. dysenteriae, S. flexnerii*); *Salmonella* (e.g. *S. typhi, S. paratyphi, S. choleraesuis, S. enteritidis*); *Listeria* (e.g. *L. monocytogenes*); *Helicobacter* (e.g. *H. pylori*); *Pseudomonas* (e.g. *P. aeruginosa*); *Staphylococcus* (e.g. *S. aureus, S. epidermidis*); *Enterococcus* (e.g. *E. faecalis, E. faecium*), *Clostridium* (e.g. *C. tetani, C. botulinum, C. difficile*); *Bacillus* (e.g. *B. anthracis*); *Corynebacterium* (e.g. *C. diphtheriae*), and *Chlamydia* (e.g. *C. trachomatis, C. pneumoniae, C. psittaci*). Representative examples of parasite pathogens include *Plasmodium* (e.g. *P. falciparum*), *Toxoplasma* (e.g. *T. gondii*) *Leshmania* (e.g. *L. major*), *Pneumocystis* (e.g. *P. carinii*), *Trichomonas* (e.g. *T. vaginalis*), *Schisostoma* (e.g. *S. mansoni*). Representative examples of fungi include *Candida* (e.g. *C. albicans*) and *Aspergillus*.

Examples of autoimmune diseases include, but are not limited to, multiple sclerosis (MS), scleroderma, rheumatoid arthritis, autoimmune hepatitis, diabetes mellitus, ulcerative colitis, Myasthenia gravis, systemic lupus erythematosus, Graves' disease, idiopathic thrombocytopenia purpura, hemolytic anemia, multiple myositis/dermatomyositis, Hashimoto's disease, autoimmune hypocytosis, Sjogren's syndrome, angitis syndrome and drug-induced autoimmune diseases (e.g., drug-induced lupus).

Moreover, as mentioned above, the fusion protein, nucleic acid molecule, vector, infectious particle, host cell and/or composition of the present disclosure can be used as an adjuvant to enhance the immune response of an animal or human organism to a particular antigen. This particular use of the present disclosure may be made in combination with one or more transgenes or transgene products as defined above, e.g. for purposes of immunotherapy. Typically, the active agent (e.g. fusion protein, infectious particle or pharmaceutical composition of the disclosure) is administered in combination with one or more transgenes or transgene products. Accordingly, there is typically also provided a composition comprising in combination a transgene product (e.g. a viral antigen or a suicide gene product) and a fusion protein as well as a composition comprising vector(s) or viral particles encoding a transgene product and a fusion protein. The transgene and the fusion-encoding nucleic acid sequences may be expressed from the same vector or from separate vectors which may have the same origin (e.g. adenoviral vectors) or a different origin (e.g. a MVA vector encoding the particular antigen and an adenoviral vector encoding the fusion protein). The fusion protein and the transgene product (or their respective encoding vectors) can be introduced into the host cell or organism either concomitantly or sequentially either via the mucosal and/or systemic route.

Combination Therapies

The cancer treatments disclosed herein can be applied as a sole therapy or can involve conventional surgery or radiotherapy, hormonal therapy, or chemotherapy. Such chemotherapy can include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family for example EGFR family tyrosine kinase inhibitors such as: N-(3-chloro-4-fluorophenyl)-7-methoxy-6-(3-morpholinopropoxy)quinazolin-4-a mine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors of phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-RAS antisense; and (viii) immunotherapy approaches, including for example ex-vivo and in-vivo approaches to increase the immunogenicity of subject tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

The combination therapy also contemplates use of the disclosed pharmaceutical compositions with radiation therapy or surgery, as an alternative, or a supplement, to a second therapeutic or chemotherapeutic agent.

A typical chronic lymphocytic leukemia (CLL) chemotherapeutic plan includes combination chemotherapy with chlorambucil or cyclophosphamide, plus a corticosteroid such as prednisone or prednisolone. The use of a corticosteroid has the additional benefit of suppressing some related autoimmune diseases, such as immunohemolytic anemia or immune-mediated thrombocytopenia. In resistant cases, single-agent treatments with nucleoside drugs such as fludarabine, pentostatin, or cladribine may be successful. Patients may consider allogeneic or autologous bone marrow transplantation. In certain embodiments, the disclosure contemplates combination treatments using conjugates disclosed herein in combination with chloroambucil, cyclophosphamide, prednisone, prednisolone, fludarabine, pentostatin, and/or cladribine or combinations thereof.

Treatment of acute lymphoblastic leukemia typically includes chemotherapy to bring about bone marrow remission. Typical regiments include prednisone, vincristine, and an anthracycline drug, L-asparaginase or cyclophosphamide. Other options include tprednisone, L-asparaginase, and vincristine. Consolidation therapy or intensification therapy to eliminate any remaining leukemia may include antimetabolite drugs such as methotrexate and 6-mercaptopurine (6-MP). In certain embodiments, the disclosure contemplates combination treatments using conjugates disclosed herein in combination with COP, CHOP, R-CHOP, imatinib, alemtuzumab, vincristine, L-asparaginase or cyclophosphamide, methotrexate and/or 6-mercaptopurine (6-MP). COP refers to a chemotherapy regimen used in the treatment of lymphoma of cyclophosphamide, vincristine, and prednisone or prednisolone and optionally hydroxydaunorubicin (CHOP) and optionally rituximab (R-CHOP).

In some embodiments, the disclosure relates to treating a viral infection by administering a GIFT disclosed herein, e.g., GM-CSF and IL-4 conjugate in combination with a second antiviral agent. In further embodiments, a GIFT disclosed herein, e.g., GM-CSF and IL-4 conjugate is administered in combination with one or more of the following agents: abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine (AZT).

Antiviral agents include, but are not limited to, protease inhibitors (PIs), integrase inhibitors, entry inhibitors (fusion inhibitors), maturation inhibitors, and reverse transcriptase inhibitors (anti-retrovirals). Combinations of antiviral agents create multiple obstacles to viral replication, i.e., to keep the number of offspring low and reduce the possibility of a superior mutation. If a mutation that conveys resistance to one of the agents being taken arises, the other agents continue to suppress reproduction of that mutation. For example, a single anti-retroviral agent has not been demonstrated to suppress an HIV infection for long. These agents are typically taken in combinations in order to have a lasting effect. As a result, the standard of care is to use combinations of anti-retrovirals.

Reverse transcribing viruses replicate using reverse transcription, i.e., the formation of DNA from an RNA template. Retroviruses often integrate the DNA produced by reverse transcription into the host genome. They are susceptible to antiviral drugs that inhibit the reverse transcriptase enzyme. In certain embodiments the disclosure relates to methods of treating viral infections by administering a GM-CSF and IL-4 conjugate, and a retroviral agent such as nucleoside and nucleotide reverse transcriptase inhibitors (NRTI) and/or a non-nucleoside reverse transcriptase inhibitors (NNRTI). Examples of nucleoside reverse transcriptase inhibitors include zidovudine, didanosine, zalcitabine, stavudine, lamivudine, abacavir, emtricitabine, entecavir, apricitabine. Examples of nucleotide reverse transcriptase inhibitors include tenofovir and adefovir. Examples of non-nucleoside reverse transcriptase inhibitors include efavirenz, nevirapine, delavirdine, and etravirine.

In certain embodiments, the disclosure relates to methods of treating a viral infection by administering a GIFT disclosed herein, e.g., GM-CSF and IL-4 conjugate optionally with an antigen in combination with an antiviral drug, e.g., 2',3'-dideoxyinosine and a cytostatic agent, e.g., hydroxyurea.

Human immunoglobulin G (IgG) antibodies are believed to have opsonizing and neutralizing effects against certain viruses. IgG is sometimes administered to a subject diagnosed with immune thrombocytopenic purpura (ITP) secondary to a viral infection since certain viruses such as, HIV and hepatitis, cause ITP. In certain embodiments, the disclosure relates to methods of treating or preventing viral infections comprising administering a GM-CSF and IL-4 conjugate in combination with an immunoglobulin to a subject. IgG is typically manufactured from large pools of human plasma that are screened to reduce the risk of undesired virus transmission. The Fc and Fab functions of the IgG molecule are usually retained. Therapeutic IgGs include Privigen, Hizentra, and WinRho. WinRho is an immunoglobulin (IgG) fraction containing antibodies to the Rho(D) antigen (D antigen). The antibodies have been shown to increase platelet counts in Rho(D) positive subjects with ITP. The mechanism is thought to be due to the formation of anti-Rho(D) (anti-D)-coated RBC complexes resulting in Fc receptor blockade, thus sparing antibody-coated platelets.

In some embodiments, the disclosure relates to treating a bacterial infection by administering a GIFT disclosed herein, e.g., GM-CSF and IL-4 conjugate in combination with an antibiotic drug. In further embodiments, the subject is co-administered with an antibiotic selected from the group comprising of Sulfonamides, Diaminopyrimidines, Quinolones, Beta-lactam antibiotics, Cephalosporins, Tetracyclines, Notribenzene derivatives, Aminoglycosides, Macrolide antibiotics, Polypeptide antibiotics, Nitrofuran derivatives, Nitroimidazoles, Nicotinin acid derivatives, Polyene antibiotics, Imidazole derivatives or Glycopeptide, Cyclic lipopeptides, Glycylcyclines and Oxazolidinones. In further embodiments, these antibiotics include but are not limited to Sulphadiazine, Sulfones—[Dapsone (DDS) and Paraaminosalicyclic (PAS)], Sulfanilamide, Sulfamethizole, Sulfamethoxazole, Sulfapyridine, Trimethoprim, Pyrimethamine, Nalidixic acids, Norfloxacin, Ciproflaxin, Cinoxacin, Enoxacin, Gatifloxacin, Gemifloxacin, Grepafloxacin, Levofloxacin, Lomefloxacin, Moxifloxacin, Ofloxacin, Pefloxacin, Sparfloxacin, Trovafloxacin, Penicillins (Amoxicillin, Ampicillin, Azlocillin, Carbenicillin, Cloxacillin, Dicloxacillin, Flucloxacillin, Hetacillin, Oxacillin, Mezlocillin, Penicillin G, Penicillin V, Piperacillin), Cephalosporins (Cefacetrile, Cefadroxil, Cefalexin, Cefaloglycin, Cefalonium, Cefaloridin, Cefalotin, Cefapirin, Cefatrizine, Cefazaflur, Cefazedone, Cefazolin, Cefradine, Cefroxadine, Ceftezole, Cefaclor, Cefonicid, Ceforanide, Cefprozil, Cefuroxime, Cefuzonam, Cefmetazole, Cefoteta, Cefoxitin, Cefcapene, Cefdaloxime, Cefdinir, Cefditoren, Cefetamet, Cefixime, Cefmenoxime, Cefodizime, Cefoperazone, Cefotaxime, Cefotiam, Cefpimizole, Cefpiramide, Cefpodoxime, Cefteram, Ceftibuten, Ceftiofur, Ceftiolen, Ceftizoxime, Ceftriaxone, Cefoperazone, Ceftazidime, Cefepime), Moxolactam, Carbapenems (Imipenem, Ertapenem, Meropenem), Monobactams (Aztreonam), Oxytetracycline, Chlortetracycline, Clomocycline, Demeclocycline, Tetracycline, Doxycycline, Lymecycline, Meclocycline, Methacycline, Minocycline, Rolitetracycline, Chloramphenicol, Amikacin, Gentamicin, Framycetin, Kanamycin, Neomicin, Neomycin, Netilmicin, Streptomycin, Tobramycin, Azithromycin, Clarithromycin, Dirithromycin, Erythromycin, Roxithromycin, Telithromycin, Polymyxin-B, Colistin, Bacitracin, Tyrothricin Notrifurantoin, Furazolidone, Metronidazole, Tinidazole, Isoniazid, Pyrazinamide, Ethionamide, Nystatin, Amphotericin-B, Hamycin, Miconazole, Clotrimazole, Ketoconazole, Fluconazole, Rifampacin, Lincomycin, Clindamycin, Spectinomycin, Chloramphenicol, Clindamycin, Colistin, Fosfomycin, Loracarbef, Metronidazole, Nitrofurantoin, Polymyxin B, Polymyxin B Sulfate, Procain, Spectinomycin, Tinidazole, Trimethoprim, Ramoplanin, Teicoplanin, Vancomycin, Trimethoprim, Sulfamethoxazole, and/or Nitrofurantoin.

EXAMPLES

Expression of Recombinant Mouse GIFT15

The expression of a cDNA encoding mouse GIFT15 was initially tested using the pET20b (Novagen) expression vector under the control of the T7 lac promoter. A translational start codon (ATG) was inserted after the GM-CSF signal peptide (FIG. 1). Using this methodology, attempts to isolate the fusokine were unsuccessful. Western blot analysis showed that the protein did not accumulate significantly after induction with IPTG. In order to improve protein yield, the gene encoding GIFT15 was subcloned into pET16b (Novagen) vector that allows for expression of the protein as an N-terminal extension of a His-tag. The small His-tag also did not prevent the degradation of GIFT15 in the intracellular environment, and only traces of recombinant GIFT15 could be detected by immunoblot analysis.

Figure 2:
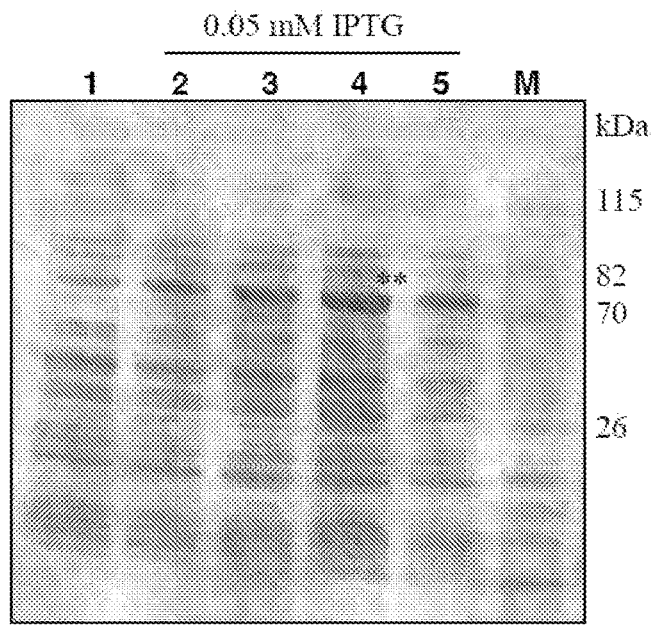
FIG. 2 shows data on the SDS-PAGE analysis of recombinant mouse GIFT15 fusion protein expression in *E. coli* Rosetta-gami™ 2(DE3)pLysS. *E. coli* harboring pHisMBP-GIFT15 was cultured at 37° C. and protein expression was induced at 25° C. (1) Cell-free extract before induction with IPTG; (2) Soluble fraction after 1 h of induction; (3) Soluble fraction after 3 h of induction; (4) Soluble fraction after 16 h of induction; (5) Total protein after overnight expression; (M) Molecular weight markers. Asterisks indicate the expression of recombinant His-MBP-GIFT15.

The liability of GIFT15 prompted us to radically modify the expression system in order to increase the amount of soluble protein and improve its stability in the bacterial intracellular milieu. The GIFT15 gene was subcloned in three different vectors that combine the expression of GIFT15 with thioredoxin (TRX), maltose-binding protein (MBP) or glutathione S-transferase (GST) (FIG. 1). Expression of these GIFT15 fusion proteins was carried out using different *E. coli* strains, growth and induction conditions, and the expression levels were evaluated by SDS-PAGE and Western blot analysis. Only the MBP fusion construct resulted in the successful overexpression of GIFT15 as soluble protein in the intracellular environment. Moreover, the amount of soluble recombinant protein increased greatly by lowering the induction temperature to 25° C. The highest level of expression was induced with 200 µM IPTG and it was significantly affected by the host *E. coli* strain. Optimal results were obtained using Rosetta-gami™ (DE3)pLysS (Novagen) (FIG. 2) cells. Although the MBP-tag forced the accumulation of soluble fusokine, this tag proved inefficient for protein purification. Additionally, non-specific cleavage of the fusion protein by the Factor Xa protease was observed. To increase the recovery of soluble MBP-GIFT15, a polyhistidine-tag was added to the N-terminal region of the MBP carrier. Furthermore, the Factor Xa protease recognition site was replaced with that of the TEV protease.

The addition of the His-Tag to the N-terminal of MBP and/or the replacement of the protease cleavage site did not influence the expression level of soluble recombinant MBP-GIFT15 (FIG. 3) and was permissive for efficient purification.

Purification of Recombinant Mouse GIFT15

Figure 3:
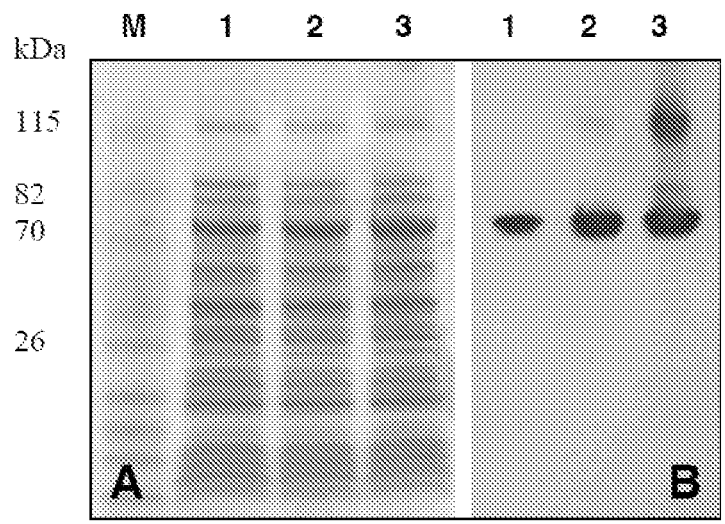
FIG. 3 shows data on the (A) SDS-PAGE and (B) Western blot analysis of His-MBP-GIFT15 expression in Rosetta-gami™ (DE3)pLysS. (1) Soluble fraction after 1 h of induction with IPTG; (2) Soluble fraction after 3 h of induction; (3) Soluble fraction after 16 h of induction. Immunodetection was conducted with anti-mouse IL-15 antibody.
Figure 4:
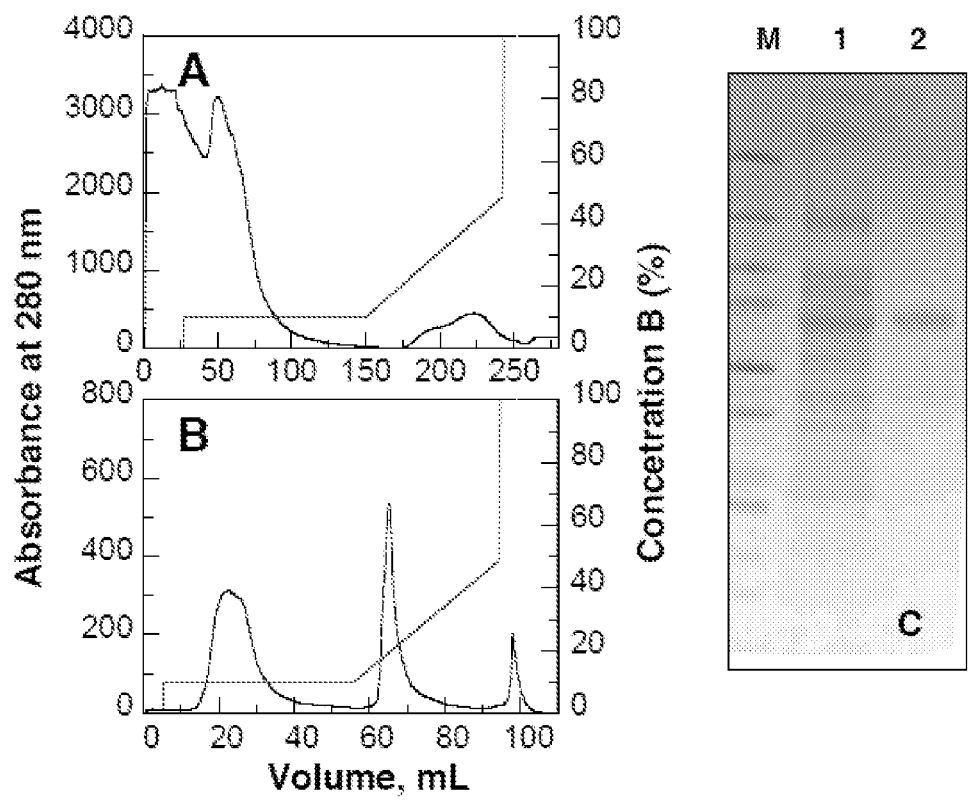
FIG. 4 shows data on the purification of His-MBP-GIFT15 on Nickel-Sepharose (A) and on DEAE-Sepharose (B) after cleavage with TEV protease. Black traces are the absorbance readings recorded at 280 nm and red traces represent the elution gradient. (C) SDS-PAGE following His-MBP-GIFT15 purification on Ni-Sepharose. (M) molecular weight markers, (1) cell free-extract, (3) His-MBP-GIFT15 after Ni-Sepharose purification.

Mouse GIFT15 was isolated using nickel-chelate chromatography as the major purification step, followed by digestion with TEV protease and anion exchange chromatography on DEAE Sepharose. The cell-free extract was loaded onto a His-Trap affinity column to bind the polyhistidine tagged recombinant GIFT15. To remove non-specific interactions between contaminating extract proteins and the matrix, the column was extensively washed with 10% buffer containing a high concentration of imidazole (buffer B). The recombinant protein was eluted with a gradient from 10 to 100% buffer B developed in 10 bed volumes. Recombinant His-MBP-GIFT15 was collected and analyzed by SDS-PAGE (FIG. 3). The solution containing the pooled fractions was concentrated and diluted in 20 mM Tris HCl, pH 8.0. The His-MBP-GIFT15 fusion was then treated for 48 h at 4° C. with TEV protease to cleave the MBP carrier from the target protein. After the cleavage reaction, the digestion mixture containing the target protein was loaded onto DEAE-Sepharose for FPLC. The column was then washed with 10% buffer B (20 mM Tris-HCl, pH 8.0, 1 M NaCl) to remove the His-MBP and TEV protease and it was developed in a linear gradient from 10% to 100% buffer B in 10 bed volumes (FIG. 4). Recombinant mouse GIFT15 eluted at a buffer B saturation of approximately 20%. The purification process described above typically yielded high purity (>90%) protein samples with an average of 0.5 mg per 1 L of culture of endotoxin-free fusokine.

Endotoxin Removal and Desalting

Protein solutions containing endotoxins were treated with 1% Triton X-114 on ice. The solutions were then warmed to 37° C., whereupon two phases formed. The Triton X-114 phase, containing the endotoxins, was separated by centrifugation at 3000×g for 15 min. Three rounds of phase separation reduced the endotoxin content by 95-97% and less than 2.5 EU/mg could be detected using an LAL Chromogenic Endotoxin Quantitation Kit (Pierce). The small amount of detergent that remained in the protein solutions was removed by gel filtration on PD-10 columns equilibrated in phosphate buffered saline. The final preparation was filter sterilized with a 0.22 m syringe filter. Western blot analysis was performed on the final sample to quantify the amount of recombinant GIFT15 by using recombinant mouse IL-15 or recombinant mouse GM-CSF as standards (FIG. 5).

Biological Activity of rGIFT15

Figure 6:
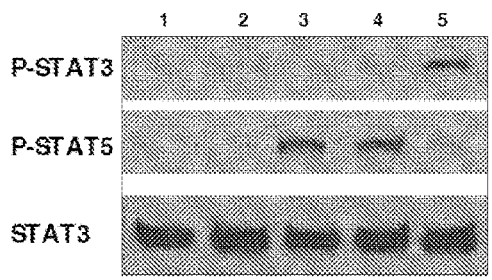
FIG. 6 shows data on STAT3/5 phosphorylation in purified B cells. Purified B cells were stimulated for 1 h with (1) PBS or 30 pmol of (2) rIL-15, (3) rGM-CSF, (4) or both cytokines and (5) rGIFT15, and cell lysate was probed for the phosphorylation status of STAT3/5. Total STAT3 protein was used as a loading control.

To test the functional activity of rGIFT15, purified mouse splenic B cells were stimulated with the bacterially expressed, recombinant GIFT15. On a molecular level, GIFT15 binds aberrantly to the trimeric IL-15 receptor (IL-15R), and as a result, asymmetrical signaling takes place downstream of the IL-15R, leading to hyperactivation of STAT3 and a hypo-STAT5 responses. Purified B cells collected from normal C57Bl/6 mice were utilized as GIFT15 responder cells. The phosphorylation status of STAT proteins following GIFT15 stimulation was investigated. Media containing 30 pmol cytokines was used to stimulate splenocytes for 1 h and cell lysates were used for Western blot analysis with antibodies specific to phosphorylated STAT proteins (FIG. 6).

rGIFT15-induced Bregs

Figure 7:
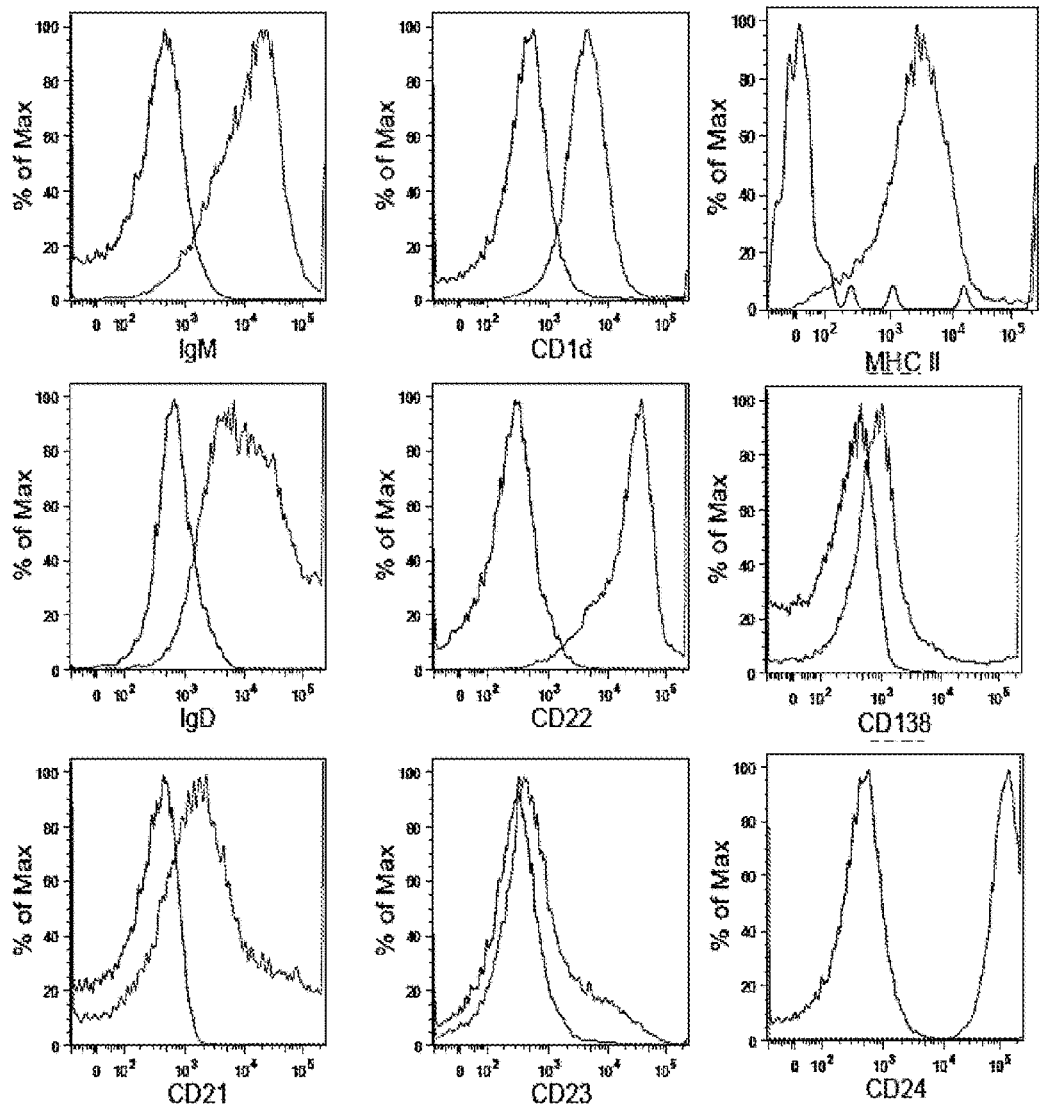
FIG. 7 shows date on the FACS analysis of B cells purified from normal C57Bl/6 mice and then cultured for 5 d in the presence of rGIFT15. Blue line is the antibody isotype control; red line is the primary antibody.

GIFT15 possesses immunosuppressive properties and reprograms naïve B cells into regulatory B cells. rGIFT15-stimulated splenic B cells produce IL-10 in vitro. To identify the phenotype of the rGIFT15-treated lymphomyeloid cells, splenocytes collected from C57BL/6 (B6) mice were cultured for 5 d in the presence of GIFT15. To determine the phenotype of rGIFT15-treated B cells, cells were analyzed for the expression of surface B cell markers (FIG. 7). rGIFT15-treated B cells were positive for Cd1d, CD21, CD22, CD23, CD24, CD138, IgM, IgD and MHC II marker proteins. The immune suppressive properties of Bregs arise from the secretion of soluble inhibitory factor IL-10. A mouse IL-10 ELISA was used to demonstrate the ability of GIFT15-derived Bregs to secrete IL-10 into the supernatant of the culture medium. Significant amounts of IL-10 were detected when B cells were cultured with recombinant GIFT15. The amount of IL-10 detected was 0.5±0.04 ng/mL in comparison to the negligible amount detected in cells treated only with PBS.

Construction of Vectors for Expression of GIFT15.

The open reading frame of GIFT15, devoid of the GM-CSF signal peptide, was amplified by PCR from a retroviral vector containing his cDNA using Phusion Hot Start Flex DNA Polymerase (NE BioLabs) and subcloned in different expression vectors. Vector-compatible primers harboring specific restriction enzyme recognition sites (NdeI-5' and XhoI-3' for pET20b/pET16b, BamHI-5' and XhoI-3' for pET32a/pET49b and EcoRI-5' and PstI-3' for pMalC4x) were designed and commercially synthesized (Integrated DNA Technologies, Coralville, Iowa). Additional primers were designed to add a His-tag in front of the maltose binding protein and replace the Factor Xa recognition site by the one recognized by the TEV protease in pMALc4x. Tropea et al. (2009) Expression and purification of soluble His(6)-tagged TEV protease. Methods Mol Biol 498, 297-307. Purified PCR fragments (QIAquick PCR Purification Kit) were treated with 1.5 units of appropriate restriction enzymes (NE BioLabs). Vectors were also digested with appropriate restriction enzyme for 2 h at 37° C. Following gel purification, the linearized plasmids were dephosphorylated with 1 unit of Antarctic Phosphatase (NE BioLabs) at 37° C. for 1 h. The linearized vectors were then mixed with the fusokine gene (molar ratio 1:3), 1 unit T4 DNA Ligase (NE BioLabs), and incubated at 16° C. overnight. The ligation reaction was then used to transform E. coli DH5a competent cells (NEB) and positive clones were selected on Luria-Bertani (LB) agar plates supplemented with the appropriate antibiotic. After confirming the integrity of the fusokine constructs by sequencing, expression vectors were introduced into different E. coli strains for protein production.

Protein Expression Trials.

Expression of recombinant fusokine was optimized by varying bacterial growth and induction conditions. Bacterial colonies, transformed with the different expression vectors, were picked and used to inoculate 1 mL LB medium which was cultured overnight in appropriate antibiotic at 37° C. The following morning, 1 mL of each overnight culture was transferred to 50 mL of either LB, Minimal (M9) or Terrific Broth (TB) medium with antibiotics. After reaching $OD_{600}=1$, the cultures were cooled down to 25 or 18° C. or alternatively maintained at 37° C. and IPTG was added (concentration between 0.05 to 1 mM). The cultures were grown for an additional 3 to 16 h at 220 rpm. The cells were then centrifuged and the pellet was re-suspended in 5 mL of BugBuster® Master Mix (EMD Millipore). After incubation on ice for 15 minutes, the crude extract was clarified by centrifugation. These crude bacterial extracts were analyzed by polyacrylamide gel electrophoresis (SDS-PAGE) under denaturing conditions and Western blotting (see below).

Expression and Purification of GIFT15.

E. coli Rosetta-gami™ 2(DE3)pLysS cells, harboring the plasmid pHisMBP-GIFT15, were used to inoculate 50 mL of TB medium containing ampicillin (100 mg/L) and chloramphenicol (34 mg/L), at 37° C. overnight. The next day, 5 mL of the starter culture was used to inoculate 4×0.5 L of the same liquid culture medium at 37° C., 220 rpm. After the culture reached an $OD_{600}$ between 0.8 and 1 (typically 5 h), the culture temperature was lowered to 25° C. and IPTG was added to a final concentration of 0.2 mM. Expression of GIFT15 was induced for 16 h. Cells were harvested by centrifugation at 40000×g in a Sorval SS34 rotor for 20 min at 4° C. Typically, 15-20 g of wet cell paste was obtained from 2.0 L of bacterial culture. Unless otherwise stated, all protein purification steps were carried out at 4° C. Cell lysate was prepared by re-suspending cell pellets in approximately 4-5 volumes of lysis buffer (20 mM sodium phosphate pH 7.4, 20 mM imidazole, 100 mM NaCl, 1 mM PMSF, 1 mM β-mercaptoethanol and 1× BugBuster Protein Extraction Reagent—EMD Millipore) and sonicating on ice for 5 min (2 min on and 1 min off cycles). Crude extract was clarified by centrifugation at 30000×g for one hour at 4° C. All chromatography experiments were performed at 4° C. with an AKTA purifier (GE Healthcare). The cell-free extract, typically 60-80 mL, was adjusted to pH 7.4 and applied slowly onto a pre-equilibrated 5 mL HisTrap chelating HP column (GE Healthcare) charged with $Ni^{+2}$ (buffer A, 20 mM sodium phosphate pH 7.4, 10 mM imidazole, 500 mM NaCl and 1 mM β-mercaptoethanol). The column was then washed with 10 column volumes (CV) of buffer. A step gradient of 5% buffer B (20 mM sodium phosphate pH 7.4, 500 mM NaCl, 500 mM imidazole and 1 mM β-mercaptoethanol) removed further contaminant proteins. The fusokine was eluted with 150 mM of imidazole. The purified protein sample was cleaved overnight at 4° C. with TEV protease. Following the cleavage reaction, the mixture containing the target protein was concentrated and then diluted with 20 mM TRIS-HCl pH 8.0, then applied to 10 mL DEAE Sepharose in FPLC equilibrated in 20 mM Tris HCl, pH 8.0. The cleaved protein eluted at approximately 20% buffer B (20 mM TRIS-HCl pH 8.0, 1 M NaCl). The purification process described above typically yielded high purity (>95%) protein samples. To remove endotoxin, the protein solutions were treated with 1% Triton X-114 on ice. After warming the reaction to 37° C., the detergent phase containing the endotoxins was precipitated by centrifugation at 3000×g for 15 min, and the fusokine was recovered in the aqueous phase. The degree of endotoxin contamination was determined using an LAL Chromogenic Endotoxin Quantitation Kit (Pierce). The purified protein solution was then desalted on a PD-10 column (GE Healthcare) equilibrated in sterile PBS and the sample was filter sterilized prior to use.

Conversion of Naïve Splenic B Cells to Regulatory Cells.

Splenocytes were collected from normal C57Bl/6 mice and B cells were isolated following the EasySep™ Mouse B Cell Isolation Kit protocols (STEMCELL Technologies Inc., Canada). B cells were cultured in RPMI 1640 medium (Thermo Scientific, Waitham, Mass.) supplemented with 10% fetal bovine serum (Wisent Bioproducts, St. Bruno, Canada), 1% penicillin-streptomycin (Thermo Scientific), 1 mM sodium pyruvate, non-essential amino acids, 20 mM Hepes and β-mercaptoethanol (Thermo Scientific) as well as recombinant GIFT15 in a 5% CO2 incubator for 4-5 days. The phenotype of the B cells was analyzed by using a BD FACSCanto II flow cytometer (San Jose, Calif.) following incubation with the appropriate antibodies for 20 minutes at 4° C.

Expression of Murine and Human GIFT4 and GIFT15 in P. pastoris

Figure 10:
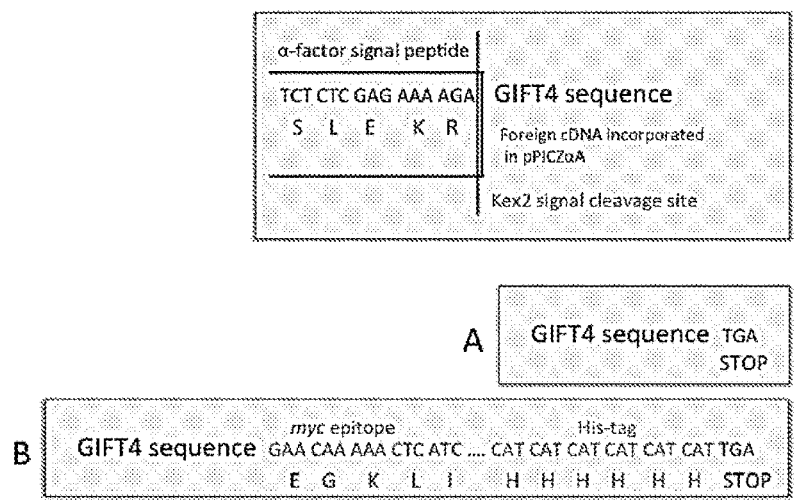
FIG. 10 shows a schematic representation of the expression system used in *P. pastoris*. (A) illustrates expression of human GIFT4 with an alpha factor signal sequence (SEQ ID NO: 23) without any tag, after cleavage (SEQ ID NO: 24) and (B) illustrates expression of GIFT4 with a myc epitope and His-tag (SEQ ID NO: 25).

The expression of two different murine and human GIFT4 constructs were assessed in P. pastoris strain X-33. These included a mature form of GIFT4 construct and a GIFT4 construct with a C-terminal hexa-histidine tag and myc epitope. For both constructs the expression of the chimeric gene is directed into the secretory pathway by the α-factor secretion signal of the pPICZαcA vector. The elements of the various constructs are shown in FIG. 10. SLEKR (SEQ ID NO: 18 Alpha factor signal peptide)—GIFT4, Kex2 cleavages sequence KR-GIFT4.

One is able to isolate a clone for the expression of the mature version of mouse GIFT4 without a C-terminal tag, e.g., myc epitope and a His-tagged. Western blotting analysis confirms sufficient expression levels in presence of 1% methanol. Unfractionated splenocytes were stimulated with yeast-derived GIFT4 for 4 days. Flow cytometer analysis of unfractionated splenocytes stimulated with yeast-derived mouse GIFT4 caused up-regulation of CD80, CD83, and CD86 similarly to what observed with the mammalian derived fusokine.

Figure 11:
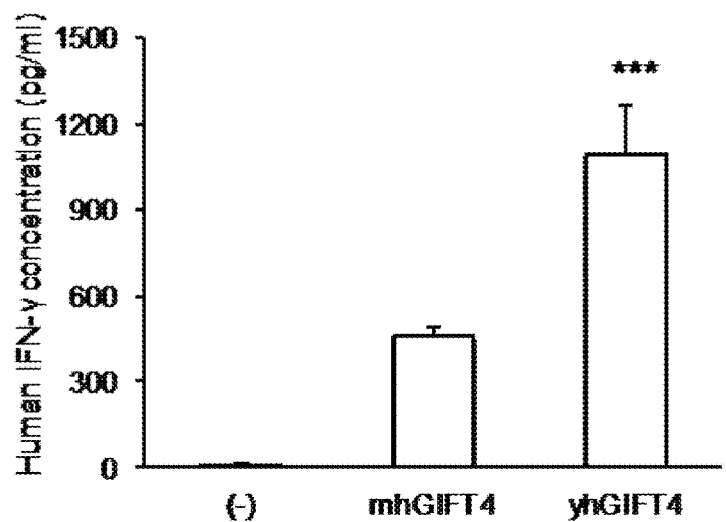
FIG. 11 shows data for IFN-γ production detected by ELISA for unfractionated human PBMCs stimulated for 7 days with either mammalian-derived human GIFT4 or yeast-derived human GIFT4 (SEQ ID NO:25).

Human GIFT4 was expressed with a C-terminus hexa-histidine tag. After purification on Nickel column, the fractions containing the target protein were pulled together, concentrated and gel-filtered in PD-10 column to the final buffer PBS. Unfractionated human PBMCs were stimulated with either mammalian-derived or human GIFT4 (positive control) or yeast-derived human GIFT4. Expression of CD40, CD80 and CD86 was assessed by flow cytometry analysis and expression of INF-γ by ELISA (FIG. 11).

Human GIFT15 was similarly expressed with a Myc epitope and HisTag. (SEQ ID NO: 19).

The invention claimed is:

1. A recombinant protein consisting of GHMAPA-RS$^{11}$PS$^{12}$PS$^{13}$T$^{14}$QPWEHVNAIQEARRLLN$^{15}$LSRDT-AAEMN$^{16}$ETVEVISEMFDLQEPTCLQTRLELYKQGLR-GSLTKLKGPLTMMASHYKQHCPPTPETSCATQIITFE-SFKENLKDFLLVGSMRISKPHLRSISIQCYLCLLLNSH-FLTEAGIHVFILGCFSAGLPKTEANWVNVISDLKKIE-DLIOSMHIDATLYTESDVHPSCKVTAMKCFLLELOV-ISLESGDASIHDTVENLIILANNSLSSNGN$^{17}$VTESGC-KECEELEEKNIKEFLQSFVHIVQMFINTS (SEQ ID NO: 12) wherein S$^{11}$, S$^{12}$, S$^{13}$, T$^{14}$, N$^{15}$, N$^{16}$, and N$^{17}$ are not conjugated to a glycan.

2. The recombinant protein of claim 1 consisting of SEQ ID NO: 12 made by the process of, expressing a pre-cleavage recombinant protein in a prokaryotic cell, wherein the pre-cleavage recombinant protein comprises a cleavage sequence E-X$^{18}$-X$^{19}$-X$^{20}$-Q-X$^{21}$-H (SEQ ID NO: 13), wherein X$^{18}$, X$^{19}$, and X$^{20}$ are independently any amino acid, and X$^{21}$ is G, and mixing the pre-cleavage recombinant protein with a tobacco etch virus (TEV) protease under conditions such that a recombinant protein with an N-terminal comprising X$^{21}$-H— is formed.

3. The recombinant protein of claim 2, wherein the cleavage sequence is ENLYFQGH (SEQ ID NO: 14).

* * * * *

SEQUENCE LISTING

<160> NUMBER OF SEQ ID NOS: 29

<210> SEQ ID NO 1
<211> LENGTH: 116
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Where X is Alanine or Glycine

```
<220> FEATURE:
<221> NAME/KEY: MISC_FEATURE
<222> LOCATION: (79)..(79)
<223> OTHER INFORMATION: Where X is Methionine or Lysine
<220> FEATURE:
<221> NAME/KEY: MISC_FEATURE
<222> LOCATION: (100)..(100)
<223> OTHER INFORMATION: Where X is Isolecine or Threonine
<220> FEATURE:
<221> NAME/KEY: MISC_FEATURE
<222> LOCATION: (106)..(106)
<223> OTHER INFORMATION: Where X is Phenylalanine or Leucine

<400> SEQUENCE: 1

Ala Pro Xaa Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Xaa Met
65                  70                  75                  80

Ala Ser His Tyr Lys Gln His Cys Pro Pro Thr Pro Glu Thr Ser Cys
                85                  90                  95

Ala Thr Gln Xaa Ile Thr Phe Glu Ser Xaa Lys Glu Asn Leu Lys Asp
            100                 105                 110

Phe Leu Leu Val
        115

<210> SEQ ID NO 2
<211> LENGTH: 116
<212> TYPE: PRT
<213> ORGANISM: Homo sapiens

<400> SEQUENCE: 2

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val
        115

<210> SEQ ID NO 3
<211> LENGTH: 116
<212> TYPE: PRT
<213> ORGANISM: Homo sapiens

<400> SEQUENCE: 3
```

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Thr Ile Thr Phe Glu Ser Phe Lys Glu Asn Leu Lys Asp
            100                 105                 110

Phe Leu Leu Val
        115

<210> SEQ ID NO 4
<211> LENGTH: 116
<212> TYPE: PRT
<213> ORGANISM: Homo sapiens

<400> SEQUENCE: 4

Ala Pro Gly Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Thr Ile Thr Phe Glu Ser Phe Lys Glu Asn Leu Lys Asp
            100                 105                 110

Phe Leu Leu Val
        115

<210> SEQ ID NO 5
<211> LENGTH: 114
<212> TYPE: PRT
<213> ORGANISM: Homo sapiens
<220> FEATURE:
<221> NAME/KEY: MISC_FEATURE
<222> LOCATION: (93)..(93)
<223> OTHER INFORMATION: Where X is Glutamate or Lysine

<400> SEQUENCE: 5

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
50                  55                  60

```
Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Xaa Lys Asn Ile
             85                  90                  95

Lys Glu Phe Leu Gln Ser Phe Val His Ile Val Gln Met Phe Ile Asn
            100                 105                 110

Thr Ser
```

```
<210> SEQ ID NO 6
<211> LENGTH: 128
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: where X is Leucine or Isoleucine or Valine
<220> FEATURE:
<221> NAME/KEY: MISC_FEATURE
<222> LOCATION: (2)..(2)
<223> OTHER INFORMATION: where X is Phenylalanie or Aspartate
<220> FEATURE:
<221> NAME/KEY: MISC_FEATURE
<222> LOCATION: (3)..(3)
<223> OTHER INFORMATION: where X is Leucine or Isoleucine or Valine
<220> FEATURE:
<221> NAME/KEY: MISC_FEATURE
<222> LOCATION: (4)..(4)
<223> OTHER INFORMATION: where X is Leucine or Cysteine
<220> FEATURE:
<221> NAME/KEY: MISC_FEATURE
<222> LOCATION: (5)..(5)
<223> OTHER INFORMATION: where X is Glycine or serine
<220> FEATURE:
<221> NAME/KEY: MISC_FEATURE
<222> LOCATION: (109)..(109)
<223> OTHER INFORMATION: where X is Glutamate or Lysine

<400> SEQUENCE: 6
```

```
Xaa Xaa Xaa Xaa Xaa Cys Phe Ser Ala Gly Leu Pro Lys Thr Glu Ala
  1               5                  10                  15

Asn Trp Val Asn Val Ile Ser Asp Leu Lys Lys Ile Glu Asp Leu Ile
             20                  25                  30

Gln Ser Met His Ile Asp Ala Thr Leu Tyr Thr Glu Ser Asp Val His
             35                  40                  45

Pro Ser Cys Lys Val Thr Ala Met Lys Cys Phe Leu Leu Glu Leu Gln
             50                  55                  60

Val Ile Ser Leu Glu Ser Gly Asp Ala Ser Ile His Asp Thr Val Glu
 65                  70                  75                  80

Asn Leu Ile Ile Leu Ala Asn Asn Ser Leu Ser Ser Asn Gly Asn Val
                 85                  90                  95

Thr Glu Ser Gly Cys Lys Glu Cys Glu Glu Leu Glu Xaa Lys Asn Ile
            100                 105                 110

Lys Glu Phe Leu Gln Ser Phe Val His Ile Val Gln Met Phe Ile Asn
        115                 120                 125
```

```
<210> SEQ ID NO 7
<211> LENGTH: 5
<212> TYPE: PRT
<213> ORGANISM: Homo sapiens

<400> SEQUENCE: 7

Val Phe Ile Leu Gly
  1               5
```

```
<210> SEQ ID NO 8
<211> LENGTH: 5
<212> TYPE: PRT
<213> ORGANISM: Homo sapiens

<400> SEQUENCE: 8

Ile Asp Leu Cys Ser
1               5

<210> SEQ ID NO 9
<211> LENGTH: 134
<212> TYPE: PRT
<213> ORGANISM: Homo sapiens

<400> SEQUENCE: 9

Val Leu Gly Thr Ile Asp Leu Cys Ser Cys Phe Ser Ala Gly Leu Pro
1               5                   10                  15

Lys Thr Glu Ala Asn Trp Val Asn Val Ile Ser Asp Leu Lys Lys Ile
                20                  25                  30

Glu Asp Leu Ile Gln Ser Met His Ile Asp Ala Thr Leu Tyr Thr Glu
            35                  40                  45

Ser Asp Val His Pro Ser Cys Lys Val Thr Ala Met Lys Cys Phe Leu
    50                  55                  60

Leu Glu Leu Gln Val Ile Ser Leu Glu Ser Gly Asp Ala Ser Ile His
65                  70                  75                  80

Asp Thr Val Glu Asn Leu Ile Ile Leu Ala Asn Asn Ser Leu Ser Ser
                85                  90                  95

Asn Gly Asn Val Thr Glu Ser Gly Cys Lys Glu Cys Glu Glu Leu Glu
            100                 105                 110

Glu Lys Asn Ile Lys Glu Phe Leu Gln Ser Phe Val His Ile Val Gln
        115                 120                 125

Met Phe Ile Asn Thr Ser
    130

<210> SEQ ID NO 10
<211> LENGTH: 134
<212> TYPE: PRT
<213> ORGANISM: Homo sapiens

<400> SEQUENCE: 10

Val Leu Gly Thr Ile Asp Leu Cys Ser Cys Phe Ser Ala Gly Leu Pro
1               5                   10                  15

Lys Thr Glu Ala Asn Trp Val Asn Val Ile Ser Asp Leu Lys Lys Ile
                20                  25                  30

Glu Asp Leu Ile Gln Ser Met His Ile Asp Ala Thr Leu Tyr Thr Glu
            35                  40                  45

Ser Asp Val His Pro Ser Cys Lys Val Thr Ala Met Lys Cys Phe Leu
    50                  55                  60

Leu Glu Leu Gln Val Ile Ser Leu Glu Ser Gly Asp Ala Ser Ile His
65                  70                  75                  80

Asp Thr Val Glu Asn Leu Ile Ile Leu Ala Asn Asn Ser Leu Ser Ser
                85                  90                  95

Asn Gly Asn Val Thr Glu Ser Gly Cys Lys Glu Cys Glu Glu Leu Glu
            100                 105                 110

Lys Lys Asn Ile Lys Glu Phe Leu Gln Ser Phe Val His Ile Val Gln
        115                 120                 125

Met Phe Ile Asn Thr Ser
```

<210> SEQ ID NO 11
<211> LENGTH: 161
<212> TYPE: PRT
<213> ORGANISM: Homo sapiens

<400> SEQUENCE: 11

```
Arg Ile Ser Lys Pro His Leu Arg Ser Ile Ser Ile Gln Cys Tyr Leu
1               5                   10                  15

Cys Leu Leu Leu Asn Ser His Phe Leu Thr Glu Ala Gly Ile His Val
            20                  25                  30

Phe Ile Leu Gly Cys Phe Ser Ala Gly Leu Pro Lys Thr Glu Ala Asn
        35                  40                  45

Trp Val Asn Val Ile Ser Asp Leu Lys Lys Ile Glu Asp Leu Ile Gln
50                  55                  60

Ser Met His Ile Asp Ala Thr Leu Tyr Thr Glu Ser Asp Val His Pro
65                  70                  75                  80

Ser Cys Lys Val Thr Ala Met Lys Cys Phe Leu Leu Glu Leu Gln Val
                85                  90                  95

Ile Ser Leu Glu Ser Gly Asp Ala Ser Ile His Asp Thr Val Glu Asn
            100                 105                 110

Leu Ile Ile Leu Ala Asn Asn Ser Leu Ser Ser Asn Gly Asn Val Thr
        115                 120                 125

Glu Ser Gly Cys Lys Glu Cys Glu Glu Leu Glu Glu Lys Asn Ile Lys
130                 135                 140

Glu Phe Leu Gln Ser Phe Val His Ile Val Gln Met Phe Ile Asn Thr
145                 150                 155                 160

Ser
```

<210> SEQ ID NO 12
<211> LENGTH: 283
<212> TYPE: PRT
<213> ORGANISM: Homo sapiens

<400> SEQUENCE: 12

```
Gly His Met Ala Pro Ala Arg Ser Pro Ser Pro Ser Thr Gln Pro Trp
1               5                   10                  15

Glu His Val Asn Ala Ile Gln Glu Ala Arg Arg Leu Leu Asn Leu Ser
            20                  25                  30

Arg Asp Thr Ala Ala Glu Met Asn Glu Thr Val Glu Val Ile Ser Glu
        35                  40                  45

Met Phe Asp Leu Gln Glu Pro Thr Cys Leu Gln Thr Arg Leu Glu Leu
50                  55                  60

Tyr Lys Gln Gly Leu Arg Gly Ser Leu Thr Lys Leu Lys Gly Pro Leu
65                  70                  75                  80

Thr Met Met Ala Ser His Tyr Lys Gln His Cys Pro Pro Thr Pro Glu
                85                  90                  95

Thr Ser Cys Ala Thr Gln Ile Ile Thr Phe Glu Ser Phe Lys Glu Asn
            100                 105                 110

Leu Lys Asp Phe Leu Leu Val Gly Ser Met Arg Ile Ser Lys Pro His
        115                 120                 125

Leu Arg Ser Ile Ser Ile Gln Cys Tyr Leu Cys Leu Leu Leu Asn Ser
130                 135                 140

His Phe Leu Thr Glu Ala Gly Ile His Val Phe Ile Leu Gly Cys Phe
145                 150                 155                 160
```

-continued

```
Ser Ala Gly Leu Pro Lys Thr Glu Ala Asn Trp Val Asn Val Ile Ser
            165                 170                 175

Asp Leu Lys Lys Ile Glu Asp Leu Ile Gln Ser Met His Ile Asp Ala
            180                 185                 190

Thr Leu Tyr Thr Glu Ser Asp Val His Pro Ser Cys Lys Val Thr Ala
            195                 200                 205

Met Lys Cys Phe Leu Leu Glu Leu Gln Val Ile Ser Leu Glu Ser Gly
            210                 215                 220

Asp Ala Ser Ile His Asp Thr Val Glu Asn Leu Ile Ile Leu Ala Asn
225                 230                 235                 240

Asn Ser Leu Ser Ser Asn Gly Asn Val Thr Glu Ser Gly Cys Lys Glu
            245                 250                 255

Cys Glu Glu Leu Glu Glu Lys Asn Ile Lys Glu Phe Leu Gln Ser Phe
            260                 265                 270

Val His Ile Val Gln Met Phe Ile Asn Thr Ser
            275                 280
```

```
<210> SEQ ID NO 13
<211> LENGTH: 8
<212> TYPE: PRT
<213> ORGANISM: Homo sapiens
<220> FEATURE:
<221> NAME/KEY: MISC_FEATURE
<222> LOCATION: (2)..(3)
<223> OTHER INFORMATION: Where X is any amino acid
<220> FEATURE:
<221> NAME/KEY: MISC_FEATURE
<222> LOCATION: (5)..(5)
<223> OTHER INFORMATION: Where X is any amino acid
<220> FEATURE:
<221> NAME/KEY: MISC_FEATURE
<222> LOCATION: (7)..(7)
<223> OTHER INFORMATION: Where X is Glycine or Serine

<400> SEQUENCE: 13

Glu Xaa Xaa Tyr Xaa Gln Xaa His
1               5
```

```
<210> SEQ ID NO 14
<211> LENGTH: 8
<212> TYPE: PRT
<213> ORGANISM: Homo sapiens

<400> SEQUENCE: 14

Glu Asn Leu Tyr Phe Gln Gly His
1               5
```

```
<210> SEQ ID NO 15
<211> LENGTH: 130
<212> TYPE: PRT
<213> ORGANISM: Homo sapiens

<400> SEQUENCE: 15

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60
```

```
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser
    130

<210> SEQ ID NO 16
<211> LENGTH: 152
<212> TYPE: PRT
<213> ORGANISM: Homo sapiens

<400> SEQUENCE: 16

Gly Leu Thr Ser Gln Leu Leu Pro Pro Leu Phe Phe Leu Leu Ala Cys
 1               5                  10                  15

Ala Gly Asn Phe Val His Gly His Lys Cys Asp Ile Thr Leu Gln Glu
                20                  25                  30

Ile Ile Lys Thr Leu Asn Ser Leu Thr Glu Gln Lys Thr Leu Cys Thr
             35                  40                  45

Glu Leu Thr Val Thr Asp Ile Phe Ala Ala Ser Lys Asn Thr Thr Glu
 50                  55                  60

Lys Glu Thr Phe Cys Arg Ala Ala Thr Val Leu Arg Gln Phe Tyr Ser
 65                  70                  75                  80

His His Glu Lys Asp Thr Arg Cys Leu Gly Ala Thr Ala Gln Gln Phe
                 85                  90                  95

His Arg His Lys Gln Leu Ile Arg Phe Leu Lys Arg Leu Asp Arg Asn
            100                 105                 110

Leu Trp Gly Leu Ala Gly Leu Asn Ser Cys Pro Val Lys Glu Ala Asn
        115                 120                 125

Gln Ser Thr Leu Glu Asn Phe Leu Glu Arg Leu Lys Thr Ile Met Arg
    130                 135                 140

Glu Lys Tyr Ser Lys Cys Ser Ser
145                 150

<210> SEQ ID NO 17
<211> LENGTH: 139
<212> TYPE: PRT
<213> ORGANISM: Homo sapiens

<400> SEQUENCE: 17

Val Leu Thr Ser Ala Leu Leu Leu Cys Ser Val Ala Gly Gln Gly Cys
 1               5                  10                  15

Pro Thr Leu Ala Gly Ile Leu Asp Ile Asn Phe Leu Ile Asn Lys Met
                20                  25                  30

Gln Glu Asp Pro Ala Ser Lys Cys His Cys Ser Ala Asn Val Thr Ser
             35                  40                  45

Cys Leu Cys Leu Gly Ile Pro Ser Asp Asn Cys Thr Arg Pro Cys Phe
 50                  55                  60

Ser Glu Arg Leu Ser Gln Met Thr Asn Thr Thr Met Gln Thr Arg Tyr
 65                  70                  75                  80

Pro Leu Ile Phe Ser Arg Val Lys Lys Ser Val Glu Val Leu Lys Asn
                 85                  90                  95
```

-continued

```
Asn Lys Cys Pro Tyr Phe Ser Cys Glu Gln Pro Cys Asn Gln Thr Thr
             100                 105                 110
Ala Gly Asn Ala Leu Thr Phe Leu Lys Ser Leu Leu Glu Ile Phe Gln
        115                 120                 125
Lys Glu Lys Met Arg Gly Met Arg Gly Lys Ile
    130                 135
```

<210> SEQ ID NO 18
<211> LENGTH: 5
<212> TYPE: PRT
<213> ORGANISM: Homo sapiens

<400> SEQUENCE: 18

```
Ser Leu Glu Lys Arg
1               5
```

<210> SEQ ID NO 19
<211> LENGTH: 302
<212> TYPE: PRT
<213> ORGANISM: Homo sapiens

<400> SEQUENCE: 19

```
Ala Pro Ala Arg Ser Pro Ser Pro Ser Thr Gln Pro Trp Glu His Val
1               5                   10                  15
Asn Ala Ile Gln Glu Ala Arg Arg Leu Leu Asn Leu Ser Arg Asp Thr
            20                  25                  30
Ala Ala Glu Met Asn Glu Thr Val Glu Val Ile Ser Glu Met Phe Asp
        35                  40                  45
Leu Gln Glu Pro Thr Cys Leu Gln Thr Arg Leu Glu Leu Tyr Lys Gln
    50                  55                  60
Gly Leu Arg Gly Ser Leu Thr Lys Leu Lys Gly Pro Leu Thr Met Met
65                  70                  75                  80
Ala Ser His Tyr Lys Gln His Cys Pro Pro Thr Pro Glu Thr Ser Cys
                85                  90                  95
Ala Thr Gln Ile Ile Thr Phe Glu Ser Phe Lys Glu Asn Leu Lys Asp
            100                 105                 110
Phe Leu Leu Val Gly Ser Met Arg Ile Ser Lys Pro His Leu Arg Ser
        115                 120                 125
Ile Ser Ile Gln Cys Tyr Leu Cys Leu Leu Leu Asn Ser His Phe Leu
    130                 135                 140
Thr Glu Ala Gly Ile His Val Phe Ile Leu Gly Cys Phe Ser Ala Gly
145                 150                 155                 160
Leu Pro Lys Thr Glu Ala Asn Trp Val Asn Val Ile Ser Asp Leu Lys
                165                 170                 175
Lys Ile Glu Asp Leu Ile Gln Ser Met His Ile Asp Ala Thr Leu Tyr
            180                 185                 190
Thr Glu Ser Asp Val His Pro Ser Cys Lys Val Thr Ala Met Lys Cys
        195                 200                 205
Phe Leu Leu Glu Leu Gln Val Ile Ser Leu Glu Ser Gly Asp Ala Ser
    210                 215                 220
Ile His Asp Thr Val Glu Asn Leu Ile Ile Leu Ala Asn Asn Ser Leu
225                 230                 235                 240
Ser Ser Asn Gly Asn Val Thr Glu Ser Gly Cys Lys Glu Cys Glu Glu
                245                 250                 255
Leu Glu Glu Lys Asn Ile Lys Glu Phe Leu Gln Ser Phe Val His Ile
            260                 265                 270
```

```
Val Gln Met Phe Ile Asn Thr Ser Leu Glu Gln Lys Leu Ile Ser Glu
            275                 280                 285

Glu Asp Leu Asn Ser Ala Val Asp His His His His His His
    290                 295                 300

<210> SEQ ID NO 20
<211> LENGTH: 282
<212> TYPE: PRT
<213> ORGANISM: Homo sapiens

<400> SEQUENCE: 20

Ala Pro Thr Arg Ser Pro Ile Thr Val Thr Arg Pro Trp Lys His Val
1               5                   10                  15

Glu Ala Ile Lys Glu Ala Leu Asn Leu Leu Asp Asp Met Pro Val Thr
            20                  25                  30

Leu Asn Glu Glu Val Glu Val Val Ser Asn Glu Phe Ser Phe Lys Lys
        35                  40                  45

Leu Thr Cys Val Gln Thr Arg Leu Lys Ile Phe Glu Gln Gly Leu Arg
    50                  55                  60

Gly Asn Phe Thr Lys Leu Lys Gly Ala Leu Asn Met Thr Ala Ser Tyr
65                  70                  75                  80

Tyr Gln Thr Tyr Cys Pro Pro Thr Pro Glu Thr Asp Cys Glu Thr Gln
                85                  90                  95

Val Thr Thr Tyr Ala Asp Phe Ile Asp Ser Leu Lys Thr Phe Leu Thr
            100                 105                 110

Asp Asp Pro Gly Arg Arg Ala Ile Met Lys Ile Leu Lys Pro Tyr Met
        115                 120                 125

Arg Asn Thr Ser Ile Ser Cys Tyr Leu Cys Phe Leu Leu Asn Ser His
    130                 135                 140

Phe Leu Thr Glu Ala Gly Ile His Val Phe Ile Leu Gly Cys Val Ser
145                 150                 155                 160

Val Gly Leu Pro Lys Thr Glu Ala Asn Trp Ile Asp Val Arg Tyr Asp
                165                 170                 175

Leu Glu Lys Ile Glu Ser Leu Ile Gln Ser Ile His Ile Asp Thr Thr
            180                 185                 190

Leu Tyr Thr Asp Ser Asp Phe His Pro Ser Cys Lys Val Thr Ala Met
        195                 200                 205

Asn Cys Phe Leu Leu Glu Leu Gln Val Ile Leu His Glu Tyr Ser Asn
    210                 215                 220

Met Thr Leu Asn Glu Thr Val Arg Asn Val Leu Tyr Leu Ala Asn Ser
225                 230                 235                 240

Thr Leu Ser Ser Asn Lys Asn Val Ala Glu Ser Gly Cys Lys Glu Cys
                245                 250                 255

Glu Glu Leu Glu Glu Lys Thr Phe Thr Glu Phe Leu Gln Ser Phe Ile
            260                 265                 270

Arg Ile Val Gln Met Phe Ile Asn Thr Ser
        275                 280

<210> SEQ ID NO 21
<211> LENGTH: 284
<212> TYPE: PRT
<213> ORGANISM: Homo sapiens

<400> SEQUENCE: 21

Gly His Ala Pro Thr Arg Ser Pro Ile Thr Val Thr Arg Pro Trp Lys
1               5                   10                  15
```

```
His Val Glu Ala Ile Lys Glu Ala Leu Asn Leu Leu Asp Asp Met Pro
            20                  25                  30

Val Thr Leu Asn Glu Glu Val Glu Val Ser Asn Glu Phe Ser Phe
        35                  40                  45

Lys Lys Leu Thr Cys Val Gln Thr Arg Leu Lys Ile Phe Glu Gln Gly
50                  55                  60

Leu Arg Gly Asn Phe Thr Lys Leu Lys Gly Ala Leu Asn Met Thr Ala
65                  70                  75                  80

Ser Tyr Tyr Gln Thr Tyr Cys Pro Pro Thr Pro Glu Thr Asp Cys Glu
                85                  90                  95

Thr Gln Val Thr Thr Tyr Ala Asp Phe Ile Asp Ser Leu Lys Thr Phe
            100                 105                 110

Leu Thr Asp Asp Pro Gly Arg Arg Ala Ile Met Lys Ile Leu Lys Pro
        115                 120                 125

Tyr Met Arg Asn Thr Ser Ile Ser Cys Tyr Leu Cys Phe Leu Leu Asn
    130                 135                 140

Ser His Phe Leu Thr Glu Ala Gly Ile His Val Phe Ile Leu Gly Cys
145                 150                 155                 160

Val Ser Val Gly Leu Pro Lys Thr Glu Ala Asn Trp Ile Asp Val Arg
                165                 170                 175

Tyr Asp Leu Glu Lys Ile Glu Ser Leu Ile Gln Ser Ile His Ile Asp
            180                 185                 190

Thr Thr Leu Tyr Thr Asp Ser Asp Phe His Pro Ser Cys Lys Val Thr
        195                 200                 205

Ala Met Asn Cys Phe Leu Leu Glu Leu Gln Val Ile Leu His Glu Tyr
    210                 215                 220

Ser Asn Met Thr Leu Asn Glu Thr Val Arg Asn Val Leu Tyr Leu Ala
225                 230                 235                 240

Asn Ser Thr Leu Ser Ser Asn Lys Asn Val Ala Glu Ser Gly Cys Lys
                245                 250                 255

Glu Cys Glu Glu Leu Glu Glu Lys Thr Phe Thr Glu Phe Leu Gln Ser
            260                 265                 270

Phe Ile Arg Ile Val Gln Met Phe Ile Asn Thr Ser
        275                 280

<210> SEQ ID NO 22
<211> LENGTH: 280
<212> TYPE: PRT
<213> ORGANISM: Homo sapiens

<400> SEQUENCE: 22

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110
```

```
Phe Leu Leu Val Gly Ser Met Arg Ile Ser Lys Pro His Leu Arg Ser
        115                 120                 125

Ile Ser Ile Gln Cys Tyr Leu Cys Leu Leu Leu Asn Ser His Phe Leu
    130                 135                 140

Thr Glu Ala Gly Ile His Val Phe Ile Leu Gly Cys Phe Ser Ala Gly
145                 150                 155                 160

Leu Pro Lys Thr Glu Ala Asn Trp Val Asn Val Ile Ser Asp Leu Lys
                165                 170                 175

Lys Ile Glu Asp Leu Ile Gln Ser Met His Ile Asp Ala Thr Leu Tyr
            180                 185                 190

Thr Glu Ser Asp Val His Pro Ser Cys Lys Val Thr Ala Met Lys Cys
        195                 200                 205

Phe Leu Leu Glu Leu Gln Val Ile Ser Leu Glu Ser Gly Asp Ala Ser
    210                 215                 220

Ile His Asp Thr Val Glu Asn Leu Ile Ile Leu Ala Asn Asn Ser Leu
225                 230                 235                 240

Ser Ser Asn Gly Asn Val Thr Glu Ser Gly Cys Lys Glu Cys Glu Glu
                245                 250                 255

Leu Glu Glu Lys Asn Ile Lys Glu Phe Leu Gln Ser Phe Val His Ile
            260                 265                 270

Val Gln Met Phe Ile Asn Thr Ser
        275                 280

<210> SEQ ID NO 23
<211> LENGTH: 366
<212> TYPE: PRT
<213> ORGANISM: Homo sapiens

<400> SEQUENCE: 23

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Ala Pro Ala Arg Ser Pro Ser Pro Ser Thr Gln
                85                  90                  95

Pro Trp Glu His Val Asn Ala Ile Gln Glu Ala Arg Arg Leu Leu Asn
            100                 105                 110

Leu Ser Arg Asp Thr Ala Ala Glu Met Asn Glu Thr Val Glu Val Ile
        115                 120                 125

Ser Glu Met Phe Asp Leu Gln Glu Pro Thr Cys Leu Gln Thr Arg Leu
    130                 135                 140

Glu Leu Tyr Lys Gln Gly Leu Arg Gly Ser Leu Thr Lys Leu Lys Gly
145                 150                 155                 160

Pro Leu Thr Met Met Ala Ser His Tyr Lys Gln His Cys Pro Pro Thr
                165                 170                 175

Pro Glu Thr Ser Cys Ala Thr Gln Thr Ile Thr Phe Glu Ser Phe Lys
            180                 185                 190

Glu Asn Leu Lys Asp Phe Leu Leu Val Ile Pro Phe Asp Cys Trp Glu
```

```
            195                 200                 205
Pro Val Gln Glu Ser Met Gly Leu Thr Ser Gln Leu Leu Pro Leu
210                 215                 220

Phe Phe Leu Leu Ala Cys Ala Gly Asn Phe Val His Gly His Lys Cys
225                 230                 235                 240

Asp Ile Thr Leu Gln Glu Ile Ile Lys Thr Leu Asn Ser Leu Thr Glu
                245                 250                 255

Gln Lys Thr Leu Cys Thr Glu Leu Thr Val Thr Asp Ile Phe Ala Ala
                260                 265                 270

Ser Lys Asn Thr Thr Glu Lys Glu Thr Phe Cys Arg Ala Ala Thr Val
            275                 280                 285

Leu Arg Gln Phe Tyr Ser His His Glu Lys Asp Thr Arg Cys Leu Gly
            290                 295                 300

Ala Thr Ala Gln Gln Phe His Arg His Lys Gln Leu Ile Arg Phe Leu
305                 310                 315                 320

Lys Arg Leu Asp Arg Asn Leu Trp Gly Leu Ala Gly Leu Asn Ser Cys
                325                 330                 335

Pro Val Lys Glu Ala Asn Gln Ser Thr Leu Glu Asn Phe Leu Glu Arg
                340                 345                 350

Leu Lys Thr Ile Met Arg Glu Lys Tyr Ser Lys Cys Ser Ser
            355                 360                 365

<210> SEQ ID NO 24
<211> LENGTH: 281
<212> TYPE: PRT
<213> ORGANISM: Homo sapiens

<400> SEQUENCE: 24

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
        50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Thr Ile Thr Phe Glu Ser Phe Lys Glu Asn Leu Lys Asp
                100                 105                 110

Phe Leu Leu Val Ile Pro Phe Asp Cys Trp Glu Pro Val Gln Glu Ser
            115                 120                 125

Met Gly Leu Thr Ser Gln Leu Leu Pro Pro Leu Phe Phe Leu Leu Ala
130                 135                 140

Cys Ala Gly Asn Phe Val His Gly His Lys Cys Asp Ile Thr Leu Gln
145                 150                 155                 160

Glu Ile Ile Lys Thr Leu Asn Ser Leu Thr Glu Gln Lys Thr Leu Cys
                165                 170                 175

Thr Glu Leu Thr Val Thr Asp Ile Phe Ala Ala Ser Lys Asn Thr Thr
            180                 185                 190

Glu Lys Glu Thr Phe Cys Arg Ala Ala Thr Val Leu Arg Gln Phe Tyr
            195                 200                 205
```

```
Ser His His Glu Lys Asp Thr Arg Cys Leu Gly Ala Thr Ala Gln Gln
    210                 215                 220

Phe His Arg His Lys Gln Leu Ile Arg Phe Leu Lys Arg Leu Asp Arg
225                 230                 235                 240

Asn Leu Trp Gly Leu Ala Gly Leu Asn Ser Cys Pro Val Lys Glu Ala
                245                 250                 255

Asn Gln Ser Thr Leu Glu Asn Phe Leu Glu Arg Leu Lys Thr Ile Met
            260                 265                 270

Arg Glu Lys Tyr Ser Lys Cys Ser Ser
        275                 280

<210> SEQ ID NO 25
<211> LENGTH: 303
<212> TYPE: PRT
<213> ORGANISM: Homo sapiens

<400> SEQUENCE: 25

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Thr Ile Thr Phe Glu Ser Phe Lys Glu Asn Leu Lys Asp
            100                 105                 110

Phe Leu Leu Val Ile Pro Phe Asp Cys Trp Glu Pro Val Gln Glu Ser
        115                 120                 125

Met Gly Leu Thr Ser Gln Leu Leu Pro Pro Leu Phe Phe Leu Leu Ala
130                 135                 140

Cys Ala Gly Asn Phe Val His Gly His Lys Cys Asp Ile Thr Leu Gln
145                 150                 155                 160

Glu Ile Ile Lys Thr Leu Asn Ser Leu Thr Glu Gln Lys Thr Leu Cys
                165                 170                 175

Thr Glu Leu Thr Val Thr Asp Ile Phe Ala Ala Ser Lys Asn Thr Thr
            180                 185                 190

Glu Lys Glu Thr Phe Cys Arg Ala Ala Thr Val Leu Arg Gln Phe Tyr
        195                 200                 205

Ser His His Glu Lys Asp Thr Arg Cys Leu Gly Ala Thr Ala Gln Gln
210                 215                 220

Phe His Arg His Lys Gln Leu Ile Arg Phe Leu Lys Arg Leu Asp Arg
225                 230                 235                 240

Asn Leu Trp Gly Leu Ala Gly Leu Asn Ser Cys Pro Val Lys Glu Ala
                245                 250                 255

Asn Gln Ser Thr Leu Glu Asn Phe Leu Glu Arg Leu Lys Thr Ile Met
            260                 265                 270

Arg Glu Lys Tyr Ser Lys Cys Ser Ser Leu Glu Gln Lys Leu Ile Ser
        275                 280                 285

Glu Glu Asp Leu Asn Ser Ala Val Asp His His His His His His
290                 295                 300
```

<210> SEQ ID NO 26
<211> LENGTH: 127
<212> TYPE: PRT
<213> ORGANISM: Homo sapiens

<400> SEQUENCE: 26

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 27
<211> LENGTH: 133
<212> TYPE: PRT
<213> ORGANISM: Homo sapiens

<400> SEQUENCE: 27

Phe Val His Gly His Lys Cys Asp Ile Thr Leu Gln Glu Ile Ile Lys
1               5                   10                  15

Thr Leu Asn Ser Leu Thr Glu Gln Lys Thr Leu Cys Thr Glu Leu Thr
            20                  25                  30

Val Thr Asp Ile Phe Ala Ala Ser Lys Asn Thr Thr Glu Lys Glu Thr
        35                  40                  45

Phe Cys Arg Ala Ala Thr Val Leu Arg Gln Phe Tyr Ser His His Glu
    50                  55                  60

Lys Asp Thr Arg Cys Leu Gly Ala Thr Ala Gln Gln Phe His Arg His
65                  70                  75                  80

Lys Gln Leu Ile Arg Phe Leu Lys Arg Leu Asp Arg Asn Leu Trp Gly
                85                  90                  95

Leu Ala Gly Leu Asn Ser Cys Pro Val Lys Glu Ala Asn Gln Ser Thr
            100                 105                 110

Leu Glu Asn Phe Leu Glu Arg Leu Lys Thr Ile Met Arg Glu Lys Tyr
        115                 120                 125

Ser Lys Cys Ser Ser
    130

<210> SEQ ID NO 28
<211> LENGTH: 123
<212> TYPE: PRT
<213> ORGANISM: Homo sapiens

<400> SEQUENCE: 28

Leu Gln Glu Ile Ile Lys Thr Leu Asn Ser Leu Thr Glu Gln Lys Thr
1               5                   10                  15

```
Leu Cys Thr Glu Leu Thr Val Thr Asp Ile Phe Ala Ala Ser Lys Asn
            20                  25                  30

Thr Thr Glu Lys Glu Thr Phe Cys Arg Ala Ala Thr Val Leu Arg Gln
            35                  40                  45

Phe Tyr Ser His His Glu Lys Asp Thr Arg Cys Leu Gly Ala Thr Ala
            50                  55                  60

Gln Gln Phe His Arg His Lys Gln Leu Ile Arg Phe Leu Lys Arg Leu
65                  70                  75                  80

Asp Arg Asn Leu Trp Gly Leu Ala Gly Leu Asn Ser Cys Pro Val Lys
                85                  90                  95

Glu Ala Asn Gln Ser Thr Leu Glu Asn Phe Leu Glu Arg Leu Lys Thr
            100                 105                 110

Ile Met Arg Glu Lys Tyr Ser Lys Cys Ser Ser
            115                 120

<210> SEQ ID NO 29
<211> LENGTH: 144
<212> TYPE: PRT
<213> ORGANISM: Homo sapiens

<400> SEQUENCE: 29

Met Leu Leu Ala Met Val Leu Thr Ser Ala Leu Leu Leu Cys Ser Val
1               5                   10                  15

Ala Gly Gln Gly Cys Pro Thr Leu Ala Gly Ile Leu Asp Ile Asn Phe
            20                  25                  30

Leu Ile Asn Lys Met Gln Glu Asp Pro Ala Ser Lys Cys His Cys Ser
            35                  40                  45

Ala Asn Val Thr Ser Cys Leu Cys Leu Gly Ile Pro Ser Asp Asn Cys
            50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
            115                 120                 125

Leu Glu Ile Phe Gln Lys Glu Lys Met Arg Gly Met Arg Gly Lys Ile
            130                 135                 140
```